(12) United States Patent
Kanck et al.

(10) Patent No.: US 12,325,345 B2
(45) Date of Patent: Jun. 10, 2025

(54) SYSTEMS AND METHODS FOR ANALYZING CORE USING X-RAY FLUORESCENCE

(71) Applicant: Veracio Ltd, Salt Lake City, UT (US)

(72) Inventors: Peter Kanck, Belair (AU); Ry Zawadzki, Mariners Cove (AU)

(73) Assignee: Veracio Ltd., Salt Lake City, UT (US)

(*) Notice: Subject to any disclaimer, the term of this patent is extended or adjusted under 35 U.S.C. 154(b) by 0 days.

(21) Appl. No.: 18/434,175

(22) Filed: Feb. 6, 2024

(65) Prior Publication Data

US 2024/0286541 A1   Aug. 29, 2024

Related U.S. Application Data

(63) Continuation of application No. 17/390,071, filed on Jul. 30, 2021, which is a continuation of application No. 16/563,000, filed on Sep. 6, 2019, now Pat. No. 11,110,844, which is a continuation of application No. 16/331,314, filed as application No. PCT/US2017/050849 on Sep. 9, 2017, now Pat. No. 10,800,315.

(60) Provisional application No. 62/385,641, filed on Sep. 9, 2016.

(51) Int. Cl.
*B60P 3/14* (2006.01)
*B60P 1/52* (2006.01)
*G01N 23/223* (2006.01)

(52) U.S. Cl.
CPC ................ *B60P 3/14* (2013.01); *B60P 1/52* (2013.01); *G01N 23/223* (2013.01); *G01N 2223/076* (2013.01); *G01N 2223/321* (2013.01); *G01N 2223/643* (2013.01)

(58) Field of Classification Search
CPC ........... B60P 3/14; B60P 1/52; G01N 23/223; G01N 2223/076; G01N 2223/321; G01N 2223/643; G01N 2223/616; G01N 33/24
See application file for complete search history.

(56) References Cited

U.S. PATENT DOCUMENTS

| | | | |
|---|---|---|---|
| 3,025,398 A | 3/1962 | Dameron | |
| 3,373,440 A | 3/1968 | Jenkins | |
| 3,414,725 A | 12/1968 | Evans | |
| 3,567,929 A * | 3/1971 | White | E21D 23/26 378/45 |

(Continued)

FOREIGN PATENT DOCUMENTS

| | | |
|---|---|---|
| AU | 2013204184 | 10/2013 |
| AU | 2017322519 | 9/2017 |

(Continued)

OTHER PUBLICATIONS

U.S. Appl. No. 62/385,641, filed Sep. 9, 2016, Peter Kanck.

(Continued)

*Primary Examiner* — Edwin C Gunberg
(74) *Attorney, Agent, or Firm* — Ballard Spahr LLP

(57) ABSTRACT

A core analysis system having a trailer and an analysis assembly secured to the trailer. The analysis assembly includes an X-ray Fluorescence (XRF) detection subassembly defining a sample analysis area. The analysis assembly further includes a conveyor subassembly configured to selectively deliver one or more core samples to the sample analysis area of the XRF detection subassembly.

29 Claims, 26 Drawing Sheets

(56) References Cited

U.S. PATENT DOCUMENTS

| | | | |
|---|---|---|---|
| 5,134,271 | A | 7/1992 | Sondergeld |
| 5,164,590 | A | 11/1992 | Coles |
| 7,889,335 | B2 | 2/2011 | Durst |
| 10,031,148 | B2 | 7/2018 | Szudajski et al. |
| 2002/0084173 | A1 | 7/2002 | Paquette |
| 2006/0215810 | A1 | 9/2006 | Usui |
| 2010/0278302 | A1 | 11/2010 | Yokoyama |
| 2010/0324868 | A1 | 12/2010 | Russell |
| 2011/0188629 | A1 | 8/2011 | Meng |
| 2012/0046203 | A1 | 2/2012 | Walsh et al. |
| 2013/0170613 | A1 | 7/2013 | Utaka et al. |
| 2013/0182819 | A1 | 7/2013 | Dvorkin |
| 2014/0131165 | A1 | 5/2014 | Johnson |
| 2014/0294145 | A1* | 10/2014 | Hirose .............. H05G 1/025 378/45 |
| 2016/0116424 | A1* | 4/2016 | Furukawa .......... G01N 23/223 378/44 |
| 2016/0187313 | A1 | 6/2016 | Szudajski |
| 2016/0187361 | A1 | 6/2016 | Szudajski |
| 2019/0351804 | A1 | 11/2019 | Kanck |

FOREIGN PATENT DOCUMENTS

| | | | | |
|---|---|---|---|---|
| AU | 2017322519 A1 | 4/2019 | | |
| BR | 1120190045236 | 9/2017 | | |
| CA | 3035978 | 9/2017 | | |
| CA | 3035978 A1 | 3/2018 | | |
| CA | 3051493 A1 * | 8/2018 | ............ | E21B 49/00 |
| CL | 201900596 | 9/2017 | | |
| CN | 203965352 | 11/2014 | | |
| CN | 106040617 | 10/2016 | | |
| EP | 0310303 | 4/1993 | | |
| EP | 17849693.1 | 9/2017 | | |
| JP | 3696522 | 9/2005 | | |
| JP | 3698255 | 9/2005 | | |
| JP | 2009/180636 | 8/2009 | | |
| PE | 490-2019 | 9/2017 | | |
| WO | 2003001190 | 1/2003 | | |
| WO | 2008/056465 | 5/2008 | | |
| WO | 2008/068044 | 6/2008 | | |
| WO | 2009/098009 | 8/2009 | | |
| WO | 2009/101265 | 8/2009 | | |
| WO | 2011/146014 | 11/2011 | | |
| WO | WO-2011146014 A1 * | 11/2011 | ........... | E21B 25/005 |
| WO | 2012/149003 | 11/2012 | | |
| WO | PCT/US2017/050849 | 9/2017 | | |
| WO | WO-2018/049281 A1 | 3/2018 | | |
| ZA | 2019/01852 | 9/2017 | | |

OTHER PUBLICATIONS

U.S. Appl. No. 16/331,314, filed Sep. 9, 2017, Peter Kanck.
U.S. Appl. No. 16/563,000, filed Sep. 6, 2019, Peter Kanck.
U.S. Appl. No. 17/390,071, filed Jul. 31, 2021, Peter Kanck.
Wiatrowski HA and Barkay T "Monitoring of microbial metal transformations in the environment", Current Opinion in Biotechnology, 16(3), 261-268.
Estrada,E and Zagerhold,I "Development of a System for X-Ray Analysis Within the Mining Industry", Chalmers University of Technology (Department of Applied Information Technology).
Ross A, et al "A multi-sensor logger for rock cores: Methodology and preliminary results from the Matagami mining camp, Canada" Ore Geology Reviews, 53, pp. 93-111 (Sep. 2013).
Sjöqvist ASL, et al "An innovative optical and chemical drill core scanner", Sci Dril 19, pp. 13-16 (2015).
Croudace IW (editor) "Future Developments and Innovations in High-Resolution Core Scanning", Micro-XRF Studies of Sediment Cores, 627-647 (2015).
TATSCAN-F2: Non-Destructive XRF Core-Imaging Scanner (2006).
COX Analytical Systems: ITRAX, multi-function core scanning instrument (2006).
XRF Web Seminar: Module 2—Basic XRF Concepts (CLU-IN) (2008).
Geotek Ltd.: MSCL-S, Multi-Sensor Core Logger (2009).
Geotek Ltd.: MSCL-XZ, Multi-Sensor Core Logger (2009).
Geotek Ltd.: MSCL-XYZ, Multi-Sensor Core Logger (2009).
Specim: SisuRock—fully automated hyperspectral imaging system (2010).
Mobile Laboratory for the Physical, Mineralogical and Chemical Characterization of Rocks (LAMROC), Institut national de la recherche scientifique (INRS), Quebec, Canada (2103).
Diversified Well Logging, LLC : on-site XRD and XRF analysis (2014).
DeWitt: MCS-1000E Automatic Scanner (2014).
Weatherford Laboratories: MCS-1000 XRF Core Scanner (2016).
Minesense: Sortore and Beltsense belt-based mineral sensing platforms (2016).
Corescan: Hyperspectral Core Imager III (2016).
International Search Report and Written Opinion were mailed on Nov. 16, 2017 by the International Searching Authority for International Application No. PCT/US2017/050849, filed on Sep. 9, 2017 and published as WO 2018/049281 on Mar. 15, 2018 (Applicant—BLY, IP) (12 Pages).
International Preliminary Report on Patentability was mailed on Mar. 12, 2019 by the International Searching Authority for International Application No. PCT/US2017/050849, filed on Sep. 9, 2017 and published as WO 2018/049281 on Mar. 15, 2018 (Applicant—BLY, IP) (11 Pages).
Examination Report was mailed on Sep. 20, 2019 by the Australian Patent Office for AU Application No. 2017322519, which was filed on Sep. 9, 2017 (Applicant—BLY IP, Inc.) (2 pages).
Non Final Rejection was issued on Nov. 1, 2019 by the USPTO for U.S. Appl. No. 16/331,314, filed Nov. 1, 2019 and published as US 2019-0351804 A1 on Nov. 21, 2019 (Inventor—Peter Knack) (9 Pages).
Response to Non Final Rejection was mailed on Jan. 31, 2020 to the USPTO for U.S. Appl. No. 16/331,314, filed Nov. 1, 2019 and published as US 2019-0351804 A1 on Nov. 21, 2019 (Inventor—Peter Knack) (10 Pages).
Non Final Rejection was issued on Apr. 15, 2020 by the USPTO for U.S. Appl. No. 16/563,000, filed Sep. 6, 2019 (Inventor—Peter Knack).
Final Rejection was issued on Dec. 15, 2020 by the USPTO for U.S. Appl. No. 16/563,000, filed Sep. 6, 2019 (Inventor—Peter Knack).
Non Final Rejection was issued on Mar. 26, 2021 by the USPTO for U.S. Appl. No. 16/563,000, filed Sep. 6, 2019 (Inventor—Peter Knack).
Ross. P. S. et al. "A multi-sensor logger for rock cores: Methodology and preliminary results from the Matagami mining camp, Canada" Jan. 23, 2013.

* cited by examiner

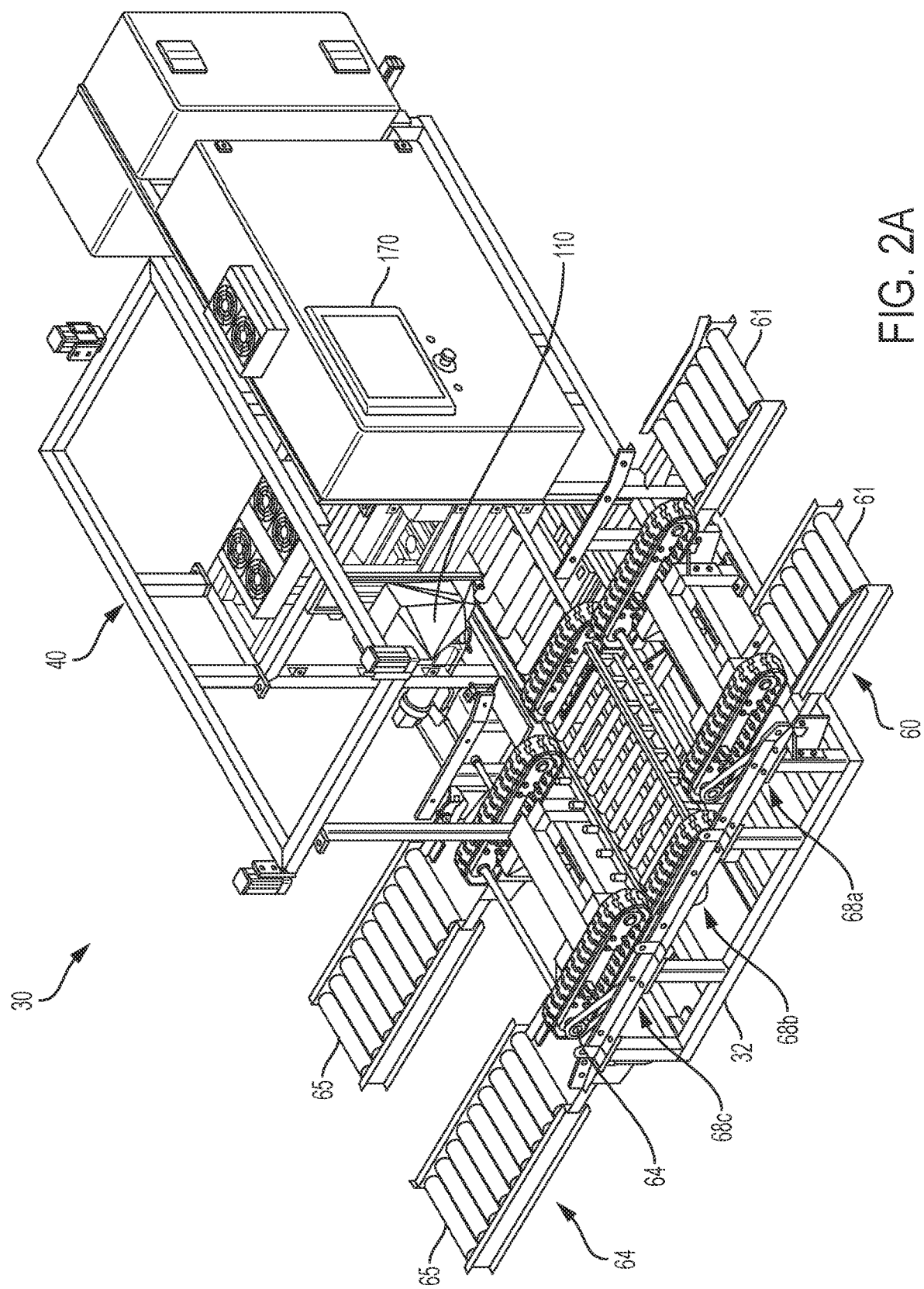

SYSTEMS AND METHODS FOR ANALYZING CORE USING X-RAY FLUORESCENCE

CROSS-REFERENCE TO RELATED APPLICATION

This application is a continuation of U.S. patent application Ser. No. 17/390,071, filed Jul. 30, 2021, which is a continuation of U.S. patent application Ser. No. 16/563,000, filed Sep. 6, 2019, which is a continuation of U.S. patent application Ser. No. 16/331,314, filed Mar. 7, 2019, now U.S. Pat. No. 10,800,315, which is a U.S. National Phase Application of International Application No. PCT/US2017/050849, filed Sep. 9, 2017, which claims priority to and the benefit of the filing date of U.S. Provisional Patent Application No. 62/385,641, filed Sep. 9, 2016. Each of these applications is hereby incorporated herein by reference in its entirety.

FIELD

The disclosed invention relates to core analysis systems and methods and, more particularly, to systems and methods for analyzing core samples using X-Ray Fluorescence (XRF).

BACKGROUND

Typically, analysis of core or rock samples requires shipping of the samples to a distant laboratory, where the samples are cut and then either crushed or scanned in a controlled environment by specially trained personnel. This analysis process is frequently associated with lengthy sample transport times, delays caused by limited access to the laboratory or limited trained personnel, and delays caused by detailed analysis and reporting. Consequently, from the time the core sample is obtained, it often takes months to complete the analysis of a core or rock sample. Thus, the core or rock analysis process is not integrated into the conventional drilling workflow process. Rather, it is a separate process that frequently encounters extensive delays.

Additionally, existing systems for analyzing core or rock samples typically require extensive user training and certification before the systems can be used. Further, although comparative core analysis methods rely on the objective consistency of the location of sample points, existing core analysis systems make it nearly impossible to repeat sampling from a consistent location. Still further, existing portable core analysis systems lack appropriate methods and sufficient precision to produce meaningful data, whereas larger, more powerful core analysis systems require installation in laboratories with controlled environments, where only trained technicians are authorized to work.

Thus, there is a need for systems and methods that address one or more of the deficiencies of known systems and methods for analyzing core or rock samples. For example, there is a need for core analysis systems and methods that are integral to the overall drilling workflow process and designed for operation by a member of the drilling team. As another example, there is a need for fully integrated, autonomous core analysis systems and methods that provide repeatable, location-identified, quantifiable sample data that can be produced in a time window (e.g., within minutes or hours) that is far less than that required to complete conventional core sample analysis.

SUMMARY

Described herein, in various aspects, is a core analysis system having a trailer and an analysis assembly that is secured to the trailer. The analysis assembly can include an XRF detection subassembly and a conveyor subassembly. The analysis assembly can define a sample analysis area, and the conveyor subassembly can be configured to selectively deliver one or more core samples to the sample analysis area. The XRF detection subassembly can define a sample analysis area. Upon positioning of a core sample on the conveyor assembly, the conveyor assembly can be activated to deliver the core sample to the sample analysis area, at which point the XRF detection subassembly can be activated.

Also described herein, in further aspects, is a core analysis method. The method can include positioning a trailer in a selected position relative to a drill location. An analysis assembly can be secured to the trailer, and the analysis assembly can have an XRF detection subassembly and a conveyor subassembly. The XRF detection subassembly can define a sample analysis area. The method can also include positioning one or more core samples on the conveyor subassembly. The method can further include activating the conveyor subassembly to selectively deliver the one or more core samples to the sample analysis area of the XRF detection subassembly. The method can still further include activating the XRF detection subassembly while the one or more core samples are positioned in the sample analysis area.

DESCRIPTION OF THE DRAWINGS

FIG. 2A is a top view of a core analysis system as disclosed herein.

FIG. 14A depicts the tray in an elevated position and the guide in a lowered position, FIG. 14B depicts the tray in a lowered position and the guide in a raised position (to effect engagement between the guide and the tray), and FIG. 14C depicts the tray in the elevated position and the guide in the raised position.

DETAILED DESCRIPTION

Figure 1A:
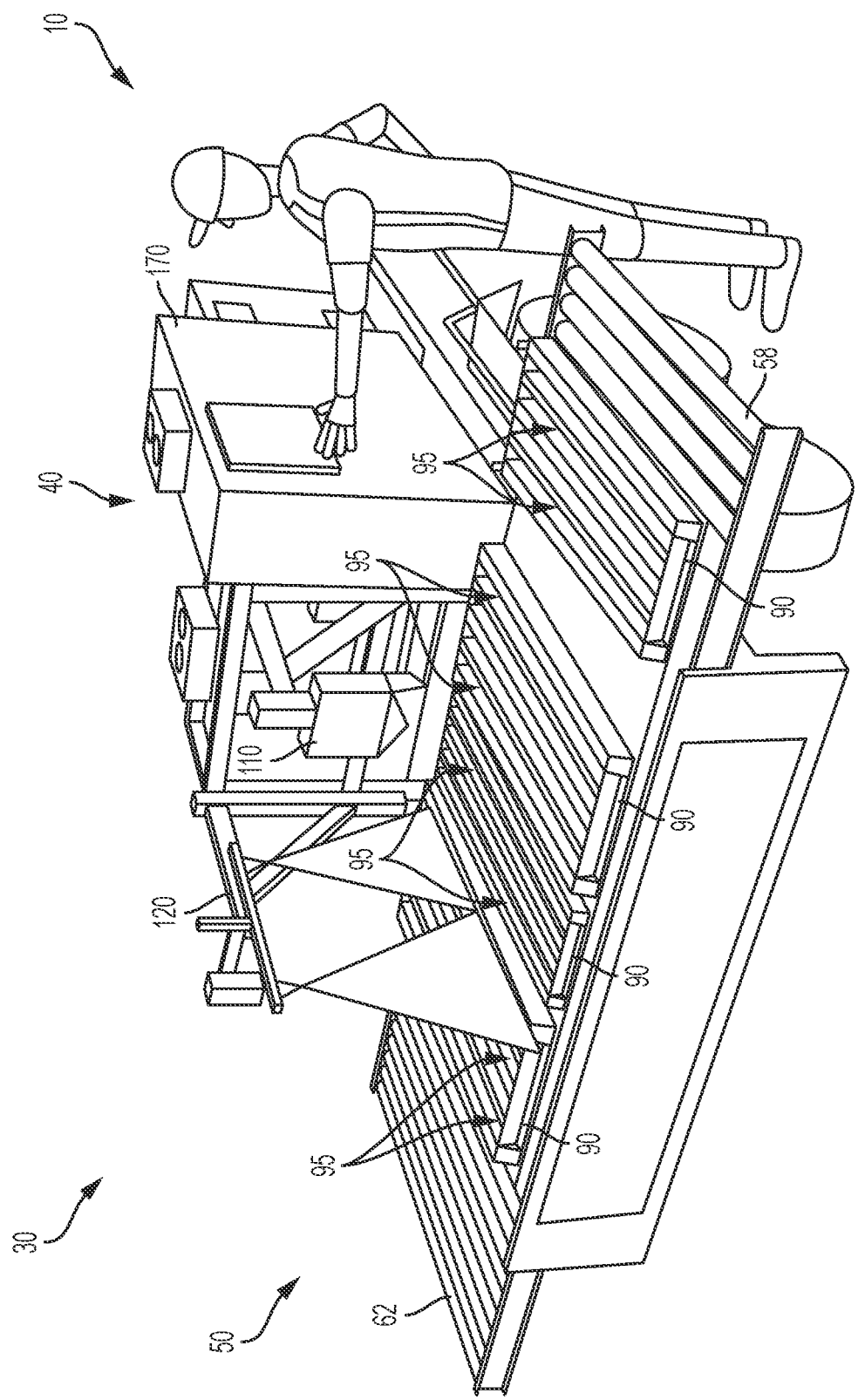
FIG. 1A is a rear perspective view of a core analysis system as disclosed herein.
Figure 1B:
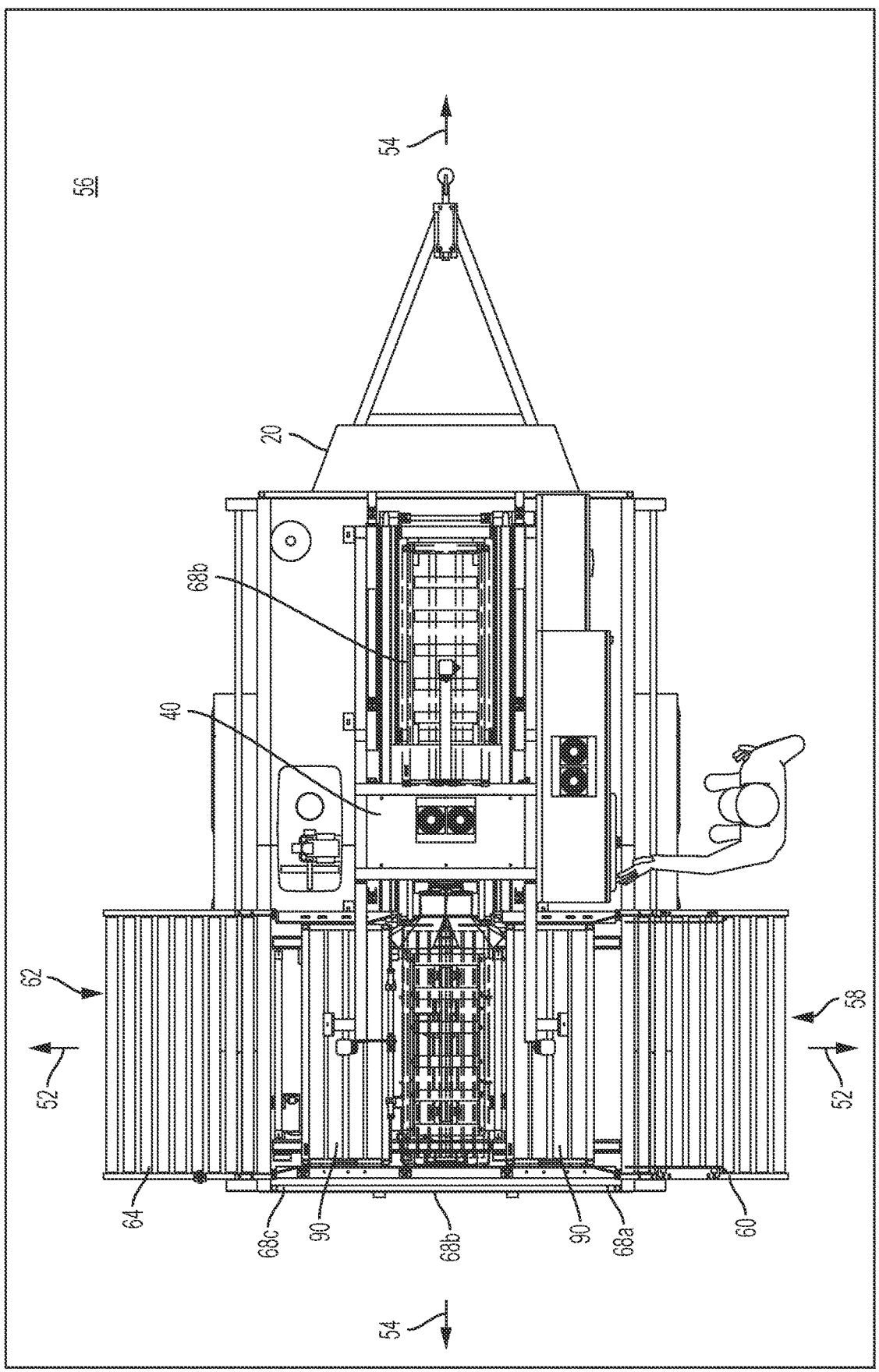
FIG. 1B is a top view of the core analysis system of FIG. 1A.
Figure 1C:
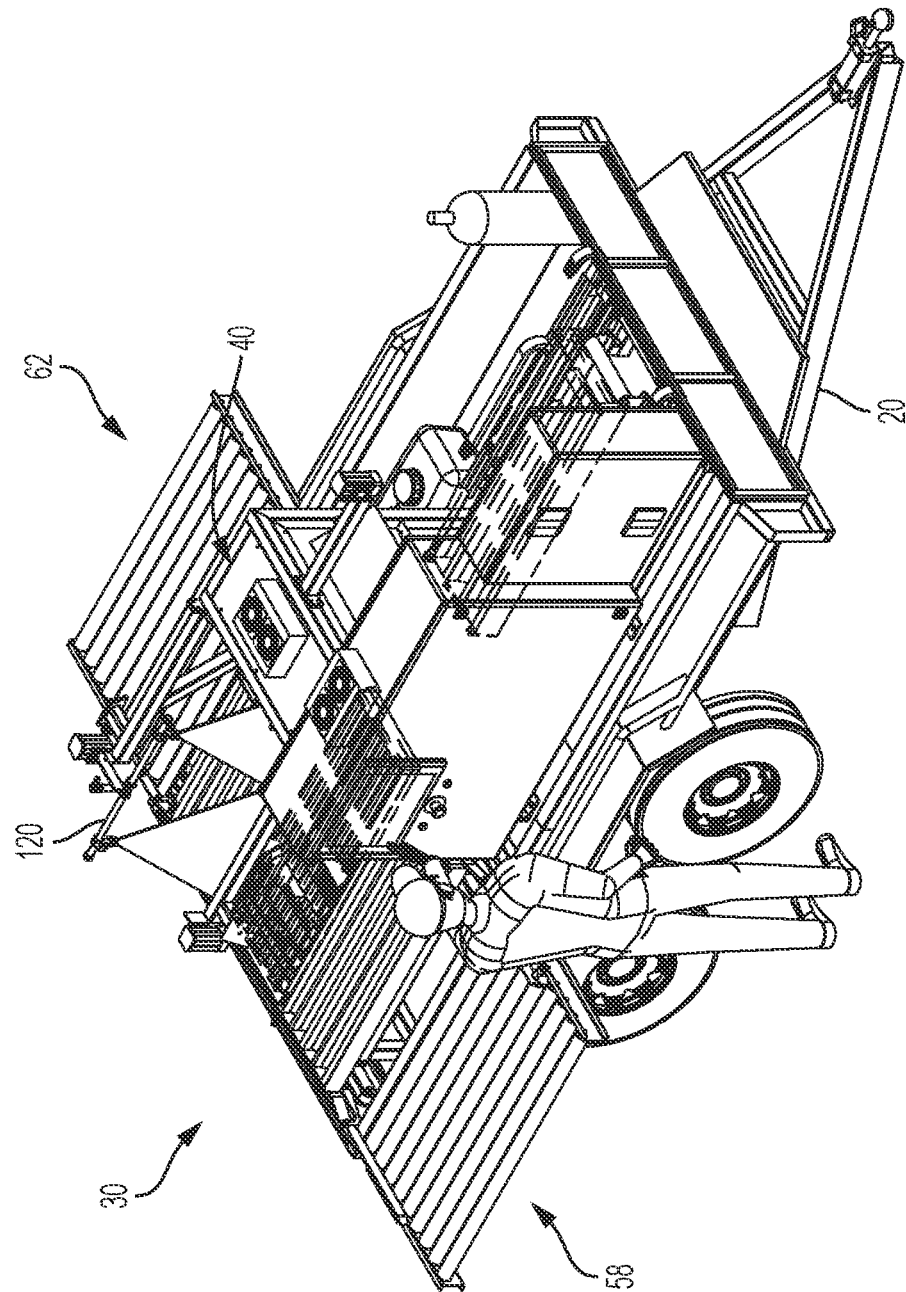
FIG. 1C is a front perspective view of the core analysis system of FIG. 1A.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a", "an", and "the" include plural referents unless the context clearly dictates otherwise. For example, use of the term "a user interface" can refer to one or more of such user interfaces, and use of the term "a sensor" can refer to one or more of such sensors.

All technical and scientific terms used herein have the same meaning as commonly understood to one of ordinary skill in the art to which this invention belongs unless clearly indicated otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

The term "substantially perpendicular" is meant to indicate that elements (e.g., axes) are perpendicular within a given plane or oriented at an angle of less than 15 degrees (optionally, less than 10 degrees) relative to each other within the given plane.

The terms "core box" and "core tray" are used interchangeably herein.

The following description supplies specific details in order to provide a thorough understanding. Nevertheless, the skilled artisan would understand that the apparatus and associated methods of using the apparatus can be implemented and used without employing these specific details. Indeed, the apparatus and associated methods can be placed into practice by modifying the illustrated apparatus and associated methods and can be used in conjunction with any other apparatus and techniques conventionally used in the industry.

Disclosed herein, in various aspects and with reference to FIGS. 1A-14C are core analysis systems and methods that are configured to provide qualitative analysis of drilled rock cores using a high-specification X-ray Fluorescence (XRF) system. In use, it is contemplated that the disclosed systems and methods can scan drilled core at required spatial intervals and within a reasonable time to permit desired on-site workflow while also providing meaningful chemo strati graphical data, which can be used by geologists and other personnel to interpret the region of drilling for additional drill targets. It is further contemplated that the analysis described herein can be completed by a member of the drilling team (e.g., a driller's assistant) in between core sampling sequences (e.g., sample pulls). Thus, it is contemplated that the disclosed system can be readily and selectively deployed in in the field and operate in at least a partially autonomous (optionally, fully autonomous) manner. In contrast to existing core analysis systems, the disclosed systems and methods can provide site-specific matrix calibration and permit the tailoring of XRF settings to elements of interest. Additionally, it is contemplated that the use of helium gas as disclosed herein can reduce X-ray attenuation, particularly for light elements (Na—Ti). More generally, it is contemplated that the disclosed system can function in an automated fashion to permit real-time acquisition of data without impacting drilling workflow.

Although generally disclosed herein as core analysis systems and methods, it is contemplated that the disclosed systems and methods can be used to analyze other material samples, such as, for example and without limitation, chips produced during reverse circulation drilling operations.

Core Analysis Systems

In exemplary aspects, and with reference to FIGS. 1-2D, 4, and 6, a core analysis system 10 can comprise an analysis assembly 30. The analysis assembly 30 can comprise a frame 32 and a plurality of components as further disclosed herein. One or more of the components of the analysis assembly can be supported by and/or secured to the frame 32 as shown in FIGS. 1A-2E. Optionally, in some aspects, the analysis assembly 30 (e.g., at least the frame 32 of the analysis assembly) can be secured to a trailer 20 using conventional means, including fasteners such as bolts, screws, clamps, and the like. In these aspects, it is contemplated that the trailer 20 can comprise conventional means for securing the trailer to a piece of drilling equipment, such as drill rig, or to a support vehicle, such as a truck, tractor, and the like. Exemplary means for securing the trailer include a hitch, one or more bolts, one or more pins, one or more arms, and the like. It is contemplated that the trailer 20 can be selectively detachable from the drilling equipment or vehicle. Thus, in use, it is contemplated that the trailer 20 can be detached from the drilling equipment or vehicle. Alternatively, it is contemplated that the trailer 20 can be permanently secured to the drilling equipment or vehicle to form a unitary or monolithic structure. In exemplary aspects, the trailer can comprise one or more front panels 22, one or more side panels 24, one or more rear panels (not shown), and one or more roof panels. In these aspects, it is contemplated that the panels can enclose the analysis assembly 30 during transport. Prior to use of the analysis assembly 30, it is contemplated that at least one side panel 24 can be removed or opened to provide access to the conveyor assembly or user interface as further disclosed herein. Optionally, it is contemplated that at least one panel 24 on each opposing side of the trailer can be removed or opened. In some exemplary aspects, at least one panel 24 on each side of the trailer can comprise a door 26 (e.g., a slide door) that can be selectively opened or closed.

Although the disclosed analysis assembly 30 is preferably secured to the trailer 20, it is contemplated that the analysis assembly 30 can also be used separately from a trailer. For example, it is contemplated that the analysis assembly 30 (e.g., at least the frame 32 of the analysis assembly) can be secured or mounted at a particular fixed location, such as a laboratory setting or other location where core samples are routinely received or delivered.

In one aspect, the analysis assembly 30 can comprise an X-ray Fluorescence (XRF) detection subassembly 40 and a conveyor subassembly 50. In this aspect, the XRF detection subassembly 40 can define a sample analysis area 42, and the conveyor subassembly 50 can be configured to selectively deliver one or more core samples to the sample analysis area.

In exemplary aspects, the XRF detection subassembly 40 can comprise an X-ray source 44 and an XRF sensor 46. In these aspects, the X-ray source 44 can be configured to deliver radiation to core samples positioned within the sample analysis area 42, and the XRF sensor 46 can be configured to detect X-ray fluorescence in response to the radiation delivered to the core samples by the X-ray source. Optionally, the XRF subassembly 40 can comprise a housing 49 that receives at least a portion of the X-ray source 44 and, optionally, at least a portion of the XRF sensor 46. The housing 49 can also include a distal aperture 45 and a window (not shown), such as a beryllium window as is known the art, which can be positioned between the aperture 45 and the XRF sensor 46 relative to a vertical axis. In exemplary aspects, it is contemplated that the XRF subassembly 40 can comprise an XRF spectrometer/analyzer as is known in the art. Optionally, in these aspects, the XRF subassembly 40 can comprise a silicon drift detector (SDD)-based XRF spectrometer/analyzer. In exemplary aspects, the aperture 45 of the housing 49 of the XRF subassembly 40 can receive (and deliver) X-rays from the X-ray source to a core sample and then receive reflected X-rays for acquiring XRF spectra using the XRF sensor 46 as further disclosed herein. Optionally, in these aspects, the XRF subassembly can further comprise a proximity sensor 47 positioned within the sample analysis area 42 for detecting the presence of a core sample in an operative position within the sample analysis area that is suitable for detecting X-ray fluorescence as further disclosed herein. Upon detecting the core sample in the operative position, the proximity sensor 47 can provide a signal to processor 80 (as further disclosed herein) that is indicative of the presence of the core sample in the operative position. In response, the processor 80 can be configured to initiate movement and activation of the components of the XRF subassembly 40 to acquire XRF spectra for the sample. Alternatively, rather than relying on the proximity sensor, the processor 80 can be configured to initiate the acquisition sequence as part of the standard movement sequence of the various actuators disclosed herein (e.g., using a PLC as further disclosed herein). In exemplary aspects, as the acquisition cycle begins, actuators 192 that are coupled to the XRF subassembly 40 can be configured to effect movement of the housing 49 until the aperture 45 (and the X-ray source, the XRF sensor, and the window) is positioned at a selected orientation relative to the sample (for example, in alignment relative to a vertical axis). Optionally, the actuators 192 can be configured to effect downward movement of the XRF subassembly 40 until the portions of a housing 49 of the assembly surrounding the aperture 45 contact the sample. Following acquisition of XRF spectra for the sample, the actuators can be configured to lift the housing 49 relative to the sample, and the housing (and aperture 45) can be translated laterally (relative to the first or second axes 52, 54) to align the aperture 45 with a second sample within the sample analysis area 42. If all samples within the sample analysis area 42 have been analyzed using the XRF subassembly 40, then the housing 49 (and aperture 45) can remain in a raised "rest" position while the conveyor subassembly 50, in response to instructions from the processor 80, initiates movement of the samples away from the sample analysis area 42 (e.g., toward the rear of the trailer).

In further exemplary aspects, it is contemplated that the XRF subassembly 40 can comprise software drivers to permit communication with other components of the system as further disclosed herein. Optionally, in these aspects, the software drivers can be configured to monitor a connection status with a processor as further disclosed herein (e.g., by monitoring an XRF subassembly broadcast packet sent periodically by the processing components). It is contemplated that the X-ray source can be controllable according to known protocols. In exemplary aspects, the voltage, amperage, or filter characteristics of the X-ray source can be selectively controllable. In exemplary aspects, the voltage of the X-ray source can range from about 6 to 50 kV. In other exemplary aspects, the amperage of the X-ray source can range from about 5 to 200 μA. It is contemplated that the filter of the X-ray source can be a film of known concentrations of elements that can be selectively adjusted. In use, it is contemplated that the voltage, amperage, and filter characteristics can be selectively adjusted to modify the emitted X-ray spectrum.

In further exemplary aspects, it is contemplated that the X-ray source 44 and the XRF sensor 46 can be placed as close as possible to the core sample. Optionally, in these aspects, it is contemplated that the X-ray source 44, the XRF sensor 46, and the window can be positioned or configured to contact (or be positioned proximate to) a core sample. Optionally, in additional exemplary aspects, it is contemplated that the X-ray source 44 and the XRF sensor 46 can be oriented and positioned such that the emitted X-rays follow a tangential path relative to the face of the core sample (at a central position on the core sample). In exemplary aspects, it is contemplated that the at least one of the X-ray source 44, the window, and the XRF sensor 46 can be at least partially received within the aperture 45 of the housing 49.

In further aspects, the conveyor subassembly 50 can be configured to selectively advance one or more core samples between a sample loading location and a sample unloading location. In these aspects, the XRF detection subassembly 40 can be positioned between the sample loading location and the sample unloading location.

In additional aspects, the conveyor subassembly can be configured to selectively advance the one or more core samples relative to a first axis 52 between the sample loading location and the sample unloading location. In these aspects, the XRF detection subassembly 40 can be positioned between the sample loading location and the sample unloading location relative to the first axis 52. In other aspects, the sample analysis area 42 of the XRF detection subassembly 40 can be spaced from the first axis 52 relative to a second axis 54. In these aspects, it is contemplated that the conveyor subassembly 50 can be configured to selectively advance the one or more core samples relative to the second axis 54 to deliver the one or more core samples to the sample analysis area 42 of the XRF detection subassembly 40. Optionally, in further aspects, within a plane 56 containing the first and second axes 52, 54, the second axis 54 can be perpendicular or substantially perpendicular to the first axis 52.

As mentioned above, in further aspects, the core analysis system 10 can further comprise a processor 80 that is communicatively coupled to the XRF detection subassembly 40. In these aspects, for each delivery of radiation to core samples positioned within the sample analysis area 42, the processor 80 can be configured to receive at least one output from the XRF sensor 46. It is contemplated that the at least one output can be indicative of the measured XRF of the core samples positioned within the sample analysis area 42. In exemplary aspects, the processor 80 can be communicatively coupled to a memory 85.

In exemplary aspects, the core analysis system 10 can further comprise at least one container 90 configured to receive one or more core samples. In these aspects, the conveyor subassembly 50 can be configured to selectively deliver the at least one container to the sample analysis area 42 of the XRF detection subassembly 40. In further exemplary aspects, each container 90 can comprise indicia 92 of at least one characteristic of the one or more core samples positioned within the container. In these aspects, it is contemplated that the core analysis system 10 can further comprise an input imaging assembly 100 that is communicatively coupled to the processor 80 and configured to detect the indicia 92 of each container 90. Optionally, in some aspects, the input imaging assembly 100 can be positioned proximate the sample loading location. Optionally, in some aspects, the indicia of each container can comprise at least one bar code, such as, for example and without limitation, a one-dimensional barcode or a two-dimensional barcode that uses QR codes. In these aspects, it is contemplated that the input imaging assembly 100 can comprise a bar code scanner. Optionally, in some aspects, the indicia of each container can comprise a radiofrequency identification (RFID) tag, such as, for example and without limitation, a close-proximity READ/WRITE card with a capacity to store at least 2 KB of data. In these aspects, it is contemplated that the input imaging assembly 100 can comprise an RFID scanner. Optionally, in further aspects, the indicia of each container can comprise standard characters (text, numbers, symbols, etc.) that are printed on or applied to the container. In these aspects, it is contemplated that the input imaging assembly 100 can comprise a camera assembly that has conventional camera hardware and image capture software for completing optical character recognition (OCR) processing of the characters positioned on the container. In use, it is contemplated that the system operator can use the user interface further disclosed herein to associate the core images produced by the camera assembly with a corresponding core sample.

In addition to detecting the indicia 92 of each container 90, the input imaging assembly 100 can acquire core images that can be used for initial processing by a system operator. Optionally, it is contemplated that the system can be configured to operate in a "Teach" mode in which the system operator uses the user interface to select areas of interest on the core images acquired by the input imaging assembly 100 to accomplish one or more of the following: (1) "Exclusion" Tagging, which excludes selected scan points while calculating or determining site sample points and point depth (i.e., appending depth), thereby addressing situations in which portions of the core samples are unscannable or otherwise deficient; (2) "Inclusion" Tagging, which selects points for a scan; or (3) "Void" Tagging, which excludes selected scan points and sample points (i.e., non-appending depth), thereby addressing situations in which the core samples include voids or core blocks. It is contemplated that the "Teach" mode can employ calculations that are performed by the application to assign the X and Y pixels inside the bounding lines to a corresponding depth (in mm). It is further contemplated that the "Teach" mode can allow for addressing a variety of different core sample conditions while maintaining quality and accuracy in depth series data. In use, it is contemplated that the operator can manipulate the selected zones using a touchscreen, stylus, or mouse, with the selected zone being depicted on the display of the human machine interface. Exemplary images of a "Teach" mode display are provided in FIGS. 7A-7B. After completing the "Teach" mode cycle, the container-specific tagging can be used to correlate data obtained during downstream analysis and processing as disclosed herein with corresponding depths that are of interest to the system operator.

Optionally, the at least one container 90 can be a core box or core tray with an upper surface that defines at least one receiving portion 95 for supporting and receiving a portion of respective drill cores during the core analysis process disclosed herein. In exemplary aspects, each core box 90 can comprise a plurality of receiving portions 95. In these aspects, it is contemplated that the plurality of receiving portions of each core box can range from about two receiving portions to about eight receiving portions. In further exemplary aspects, each receiving portion of a core box can define a diameter that is complementary to the size of a core sample obtained using coring rods of a particular size (e.g., HQ coring rods, PQ coring rods, BQ coring rods, NQ coring rods, and the like). In these aspects, it is contemplated that each core box can be shaped for use with core samples obtained from a corresponding coring rod.

In some exemplary aspects, it is contemplated that the core analysis system 10 can include a plurality of core boxes that are designed for use with a variety of different coring rod sizes. That is, it is contemplated that at least one of the core boxes can have a receiving portion with a diameter that is different than the diameter of the receiving portion of at least one other core box of the system. For example, in some exemplary aspects, the system 10 can comprise at least one core box that is configured for use with an HQ coring rod and that defines one or more receiving portions having a diameter ranging from about 60 to about 70 mm (and, more preferably, being about 65 mm). In some exemplary aspects, the system 10 can comprise at least one core box that is configured for use with a PQ coring rod and that defines one or more receiving portions having a diameter ranging from about 80 to about 90 mm (and, more preferably, being about 86.5 mm. In some exemplary aspects, the system 10 can comprise at least one core box that is configured for use with a BQ coring rod and that defines one or more receiving portions having a diameter ranging from about 35 to about 45 mm (and, more preferably, being about 38 mm). In some exemplary aspects, the system 10 can comprise at least one core box that is configured for use with an NQ coring rod and that defines one or more receiving portions having a diameter ranging from about 50 to about 60 mm (and, more preferably, being about 52.5 mm).

In exemplary aspects, it is contemplated that a plurality of core boxes provided with the system can have a consistent length (relative to a longitudinal axis of the core box) and a consistent width while having a varying height depending upon the size (e.g., diameter) of the receiving portions defined in the core box. Optionally, in these aspects, it is contemplated that the length of each core box can range from about 1,000 mm to about 1,200 mm and more preferably, from about 1,050 mm to about 1,100 mm, while the width of each core box can range from about 300 mm to about 500 mm and more preferably, from about 350 mm to about 400 mm. In exemplary aspects, it is contemplated that core boxes configured for use with HQ coring rods can have a height ranging from about 70 mm to about 90 mm and more preferably, ranging from about 75 mm to about 85 mm. It is further contemplated that core boxes configured for use with PQ coring rods can have a height ranging from about 90 mm to about 120 mm and more preferably, ranging from about 100 mm to about 110 mm. It is further contemplated that core boxes configured for use with BQ coring rods can have a height ranging from about 50 mm to about 70 mm and more preferably, ranging from about 55 mm to about 65 mm. It is still further contemplated that core boxes configured for use with NQ coring rods can have a height ranging from about 55 mm to about 85 mm and more preferably, ranging from about 65 mm to about 75 mm.

Optionally, in exemplary aspects, it is further contemplated that each of the receiving portions defined in the core box can be generally aligned with or parallel to the longitudinal axis of the core box, with the diameter of the receiving portions determining the maximum number of receiving portions that can be defined within a given core box. For example, it is contemplated that core boxes configured for use with HQ coring rods can optionally have from three to five receiving portions that are spaced apart relative to the width of the core box, with the receiving portions of such core boxes being configured to receive, in combination, from about 3 m to about 5 m (in total combined length) of core sample segments. It is further contemplated that core boxes configured for use with PQ coring rods can optionally have from two to four receiving portions that are spaced apart relative to the width of the core box, with the receiving portions of such core boxes being configured to receive, in combination, from about 2 m to about 4 m (in total combined length) of core sample segments. It is further contemplated that core boxes configured for use with BQ coring rods can optionally have from six to eight receiving portions that are spaced apart relative to the width of the core box, with the receiving portions of such core boxes being configured to receive, in combination, from about 6 m to about 8 m (in total combined length) of core sample segments. It is further contemplated that core boxes configured for use with NQ coring rods can have from four to six receiving portions that are spaced apart relative to the width of the core box, with the receiving portions of such core boxes being configured to receive, in combination, from about 4 m to about 6 m (in total combined length) of core sample segments.

In exemplary aspects, the core boxes can comprise plastic. Optionally, in some exemplary aspects, the core boxes can comprise DISCOVERER® Series 2 and 3 core sample trays manufactured by Yandina Plastics Mining Products/Total Plastics Solutions (Kunda Park, Queensland, Australia). Optionally, in other exemplary aspects, the core boxes can comprise CORITE core trays manufactured by Strength International (Keswick, South Australia). Optionally, in still further exemplary aspects, the core boxes can comprise IMPALA core trays (series 1, 2, 3, or 4) by Impala Plastics (Maddington, Western Australia).

Optionally, in exemplary aspects, the analysis system can comprise gripping elements that secure the core boxes to the conveyor subassembly 50 to permit axial movement of the core boxes as disclosed herein. In exemplary aspects, the gripping elements can be secured to portions of the conveyor subassembly 50 such that movement of the conveyor assembly effects a corresponding movement of the gripping elements (and a core box engaged by the gripping elements). Optionally, it is contemplated that the gripping elements can be provided as part of an intermediate section 68b of the conveyor assembly (as further disclosed herein) to ensure that each core box remains securely positioned in desired locations relative to the XRF detection subassembly 40 as the core box translates relative to axis 54. In these aspects, it is further contemplated that the gripping elements can be configured for selective, releasable engagement with a core box such that the core box can be selectively secured into place on the conveyor assembly and then disengaged from the conveyor assembly at an appropriate time (e.g., at the conclusion of a cycle through the XRF detection subassembly). It is contemplated that the gripping elements can comprise any conventional fastener, such as, for example and without limitation, bolts, screws, ties, projections, hooks, latches, loops, and the like, while each core box can comprise complementary engagement portions that are configured to receive or effect engagement with a portion of corresponding gripping elements. Optionally, it is contemplated that the gripping elements can be selectively moveable from a disengaged position to an engaged position, in either a manual or an automated manner (e.g., by activating an actuator under processor control). In further exemplary aspects, it is contemplated that the gripping elements can comprise a plurality of guides that can be configured to apply pressure to (e.g., apply a clamping force to) outer portions of the core box to secure the core box in a desired location and orientation.

As further disclosed herein, the disclosed analysis system can comprise mechanisms that prepare the core samples for analysis. These mechanisms can include, for example and without limitation, clearing mechanisms, drying mechanisms, and wetting mechanisms. In further aspects, the analysis system can comprise mechanisms for imaging the core samples under both dry and wet conditions. As further disclosed herein, it is contemplated that the system can provide selectable and fully automated and repeatable analysis intervals, automated data collection, and remote delivery of the completed sample analysis. A database as disclosed herein can permit storage of data corresponding to or indicative of a particular sample container (e.g., core box), a drill hole location, a sample collection date and time, calibration, sample depth, temperature, or Rh scatter intensity. In further exemplary aspects, and as disclosed herein, the system can permit remote uploading and file retrieval using a cloud-based server. The software can also permit replication of both industrial process controller (IPC) and industrial data concentrator (IDC) databases to an external USB storage option. This can then be uploaded by other (standard) means to the cloud-based server. This option can be useful in remote situations where the trailer (and the analysis assembly) is not within access of a WAN (wide area network) authentication/access service.

Figure 4:
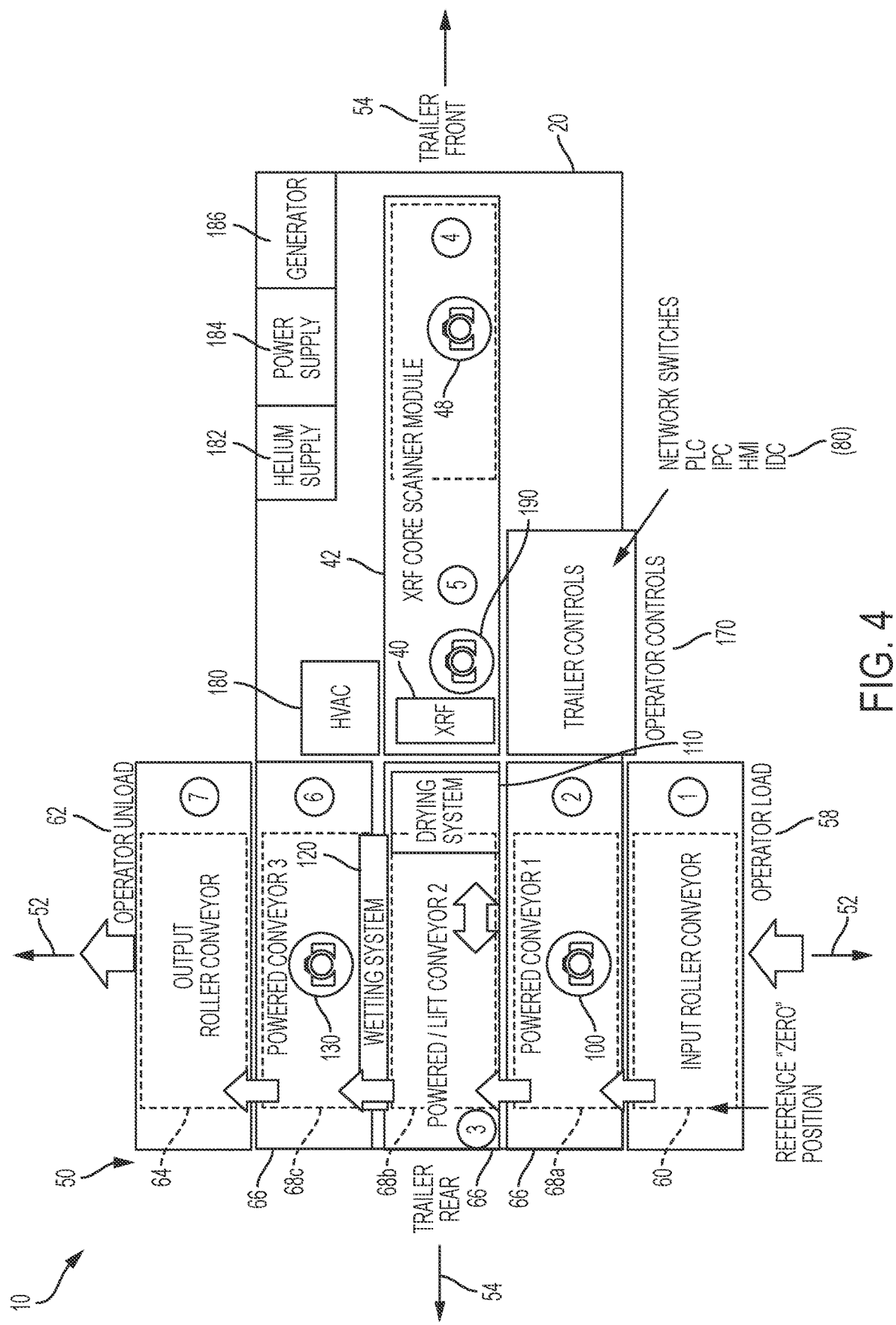
FIG. 4 is a schematic diagram depicting the flow of core samples through an exemplary core analysis system as disclosed herein.

In further exemplary aspects, and with reference to FIGS. 1A-2E and 4, the core analysis system 10 can further comprise a drying assembly 110 positioned between the sample loading location and the sample analysis area 42 of the XRF detection subassembly 40. Optionally, in exemplary aspects, the drying assembly 110 can comprise a high-velocity air knife drying system as is known in the art. Optionally, as shown in FIG. 4, in exemplary aspects, the drying assembly 110 can be placed in an elevated position proximate an entrance to the sample analysis area 42. In use, it is contemplated that the drying assembly 110 can ensure that the core samples are dry and clean before they are scanned by the XRF detection subassembly. In exemplary aspects, it is contemplated that the processor 80 can be communicatively coupled to the drying assembly 110. It is further contemplated that the processor 80 can be configured to selectively activate and deactivate the drying assembly. In further exemplary aspects, the processor 80 can be configured to activate the drying assembly such that the drying assembly operates at a selected fixed speed and at a selected fixed temperature output. Optionally, in still further exemplary aspects, the processor 80 can be configured to selectively control activation of the conveyor assembly to advance the core samples through the drying assembly 110 at a desired speed that is optimal for drying of the core samples.

In additional aspects, and with reference to FIG. 4, the XRF detection subassembly can comprise a dry-core imaging assembly 48. In these aspects, it is contemplated that the dry-core imaging assembly 48 can be configured to produce an image of core samples received within the sample analysis area 42, preferably after drying of the core samples by the drying assembly 110. Optionally, in exemplary aspects, the processor 80 can be configured to selectively activate the dry-core imaging assembly 48 to produce an image of dry core samples within the sample analysis area 42, prior to activation of the X-Ray source.

In other aspects, and with reference to FIG. 4, the XRF detection subassembly can further comprise an XRF imaging assembly 190 that is positioned to image the core samples (and their containers) after the core samples are positioned in a desired location for activation of the X-Ray source and XRF detection. It is contemplated that the images produced by the XRF imaging assembly 190 can be stored and used to determine the specific location of the core samples when XRF was detected.

In further aspects, and with reference to FIGS. 1-2D and 4, the core analysis system 10 can comprise a wetting assembly 120 positioned between the sample analysis area 42 and the sample unloading location. Optionally, in these aspects, the wetting assembly 120 can comprise a water spray mechanism as is known in the art. It is contemplated that the wetting assembly 120 can apply water (or other liquid) to the core samples to prepare the core samples for high-resolution wet imaging as further disclosed herein. In exemplary aspects, it is contemplated that the processor 80 can be communicatively coupled to the wetting assembly 120. It is further contemplated that the processor 80 can be configured to selectively activate the wetting assembly 120. Optionally, in exemplary aspects, it is contemplated that the processor 80 can be configured to activate the wetting assembly 120 such that the wetting assembly produces a desired fixed water flow rate. Optionally, in still further exemplary aspects, the processor 80 can be configured to selectively control activation of the conveyor assembly to advance the core samples through the wetting assembly 120 at a desired speed that is optimal for wetting of the core samples. In exemplary aspects, the wetting assembly 120 can comprise at least one arm and at least one nozzle positioned in fluid communication with a conduit defined within the at least one arm. In these aspects, it is contemplated that the conduit can be positioned in fluid communication with a fluid source (e.g., a pump) that is configured to pump fluid to the wetting assembly 120 in response to instructions received from the processor 80.

Optionally, in exemplary aspects, and with reference to FIG. 4, the core analysis system 10 can comprise a wet-core imaging assembly 130 positioned between the wetting assembly 120 and the sample unloading location. In these aspects, it is contemplated that the processor 80 can be communicatively coupled to the wet-core imaging assembly 130. It is further contemplated that the processor 80 can be configured to selectively activate the wet-core imaging assembly 130. In use, it is contemplated that the wet-core imaging assembly can be activated to record an image of the core samples after wetting of the core samples by the wetting assembly 120 as further disclosed herein.

In exemplary aspects, the input imaging assembly 100, the dry-core imaging assembly 48, the XRF imaging assembly 190, and the wet-core imaging assembly 130 can each comprise a respective camera assembly, such as, for example and without limitation, an IP camera. Exemplary IP cameras that are suitable for this application include LIFECAM web cameras manufactured by Microsoft Corporation (Redmond, Washington). As further disclosed herein, the camera of the input imaging assembly 100 can be used to acquire an image of a core box that allows the system operator to "tag" core images using an HMI (user interface) as further disclosed herein. As further disclosed herein, the camera of the dry-core imaging assembly 48 can be used to acquire an image of a dry core box, with the image being stored in a database as described herein. As further disclosed herein, the camera of the XRF imaging assembly 190 can be used to acquire an image of a location where XRF measurements are performed, with the image being stored in the database as described herein. As further disclosed herein, the camera of the wet-core imaging assembly 130 can be used to acquire an image of a core box after the core box has been wetted by the wetting assembly 120, with the image being stored in a database as described herein. As shown in FIGS. 1A-2D, it is contemplated that cameras of the input imaging assembly 100, the dry-core imaging assembly 48, and the wet-core imaging assembly 130 can be mounted to the frame 32 at respective locations above the core box movement pathway. As shown in FIG. 2E, it is contemplated that the camera of the XRF imaging assembly 190 can be positioned within the sample analysis area (optionally, within or coupled to housing 49). In further exemplary aspects, the disclosed IP cameras can be controlled through Ethernet connection using a trailer control network ("TrailerControlNet") as disclosed herein and shown in FIG. 5.

Figure 2B:
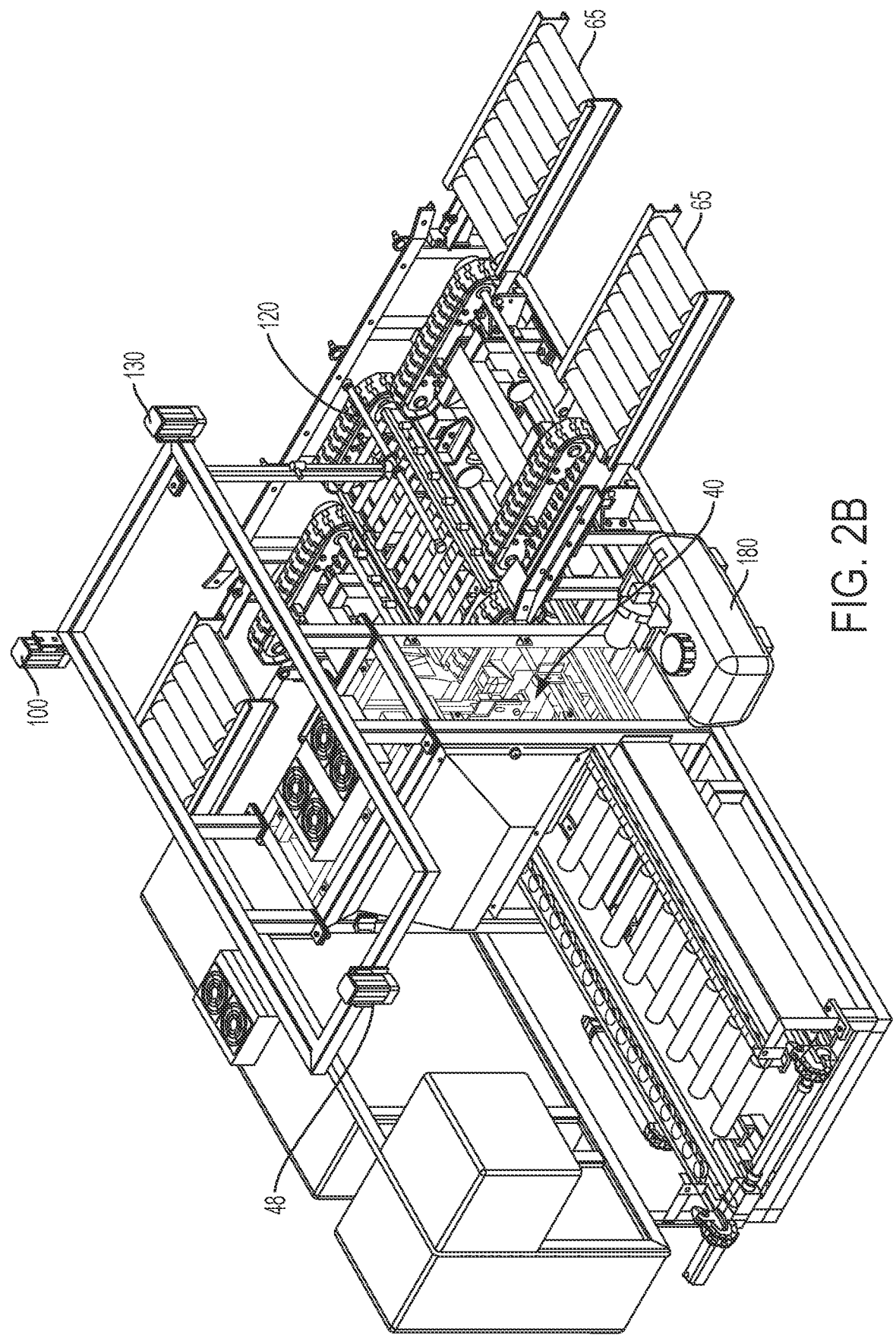
FIG. 2B is a side perspective view of the core analysis system of FIG. 2A.
Figure 2C:
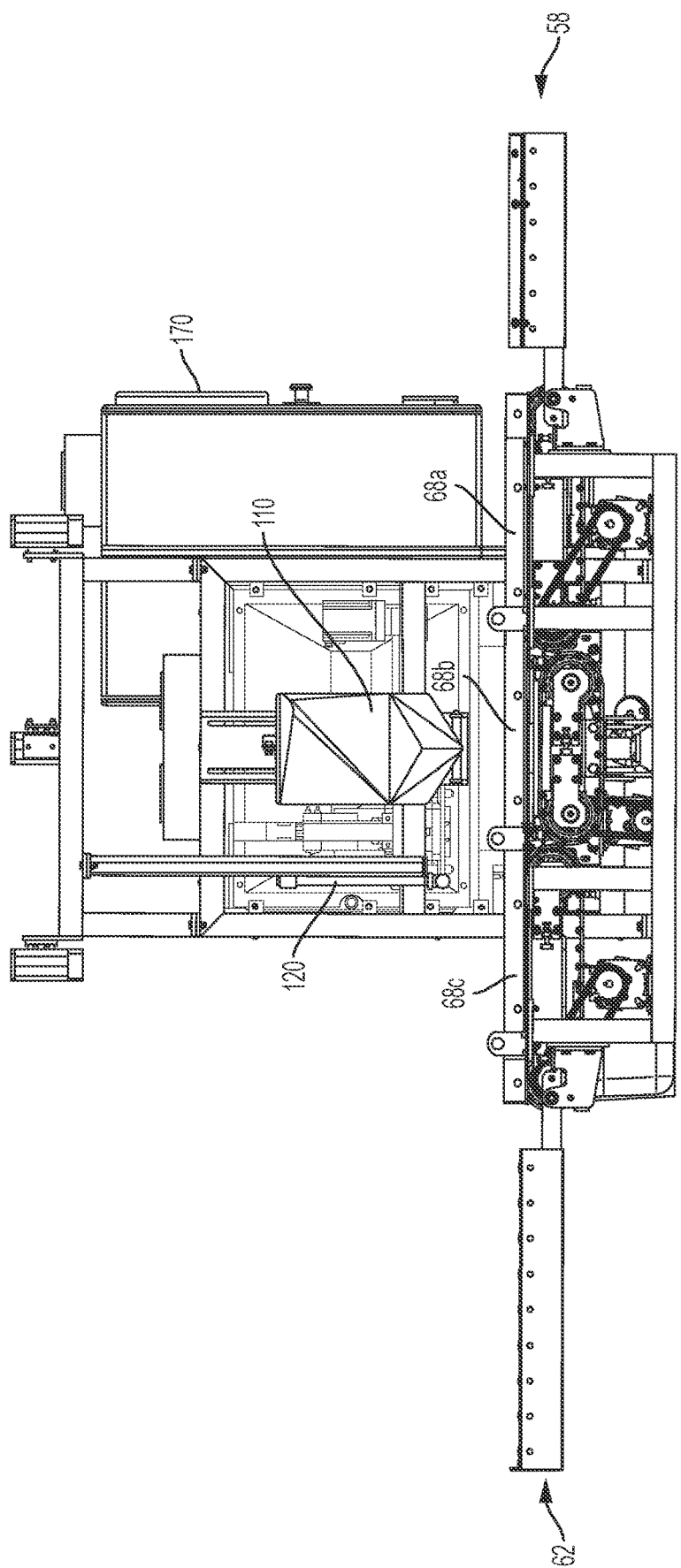
FIG. 2C is a left side elevational view of the core analysis system of FIG. 2A.
Figure 2D:
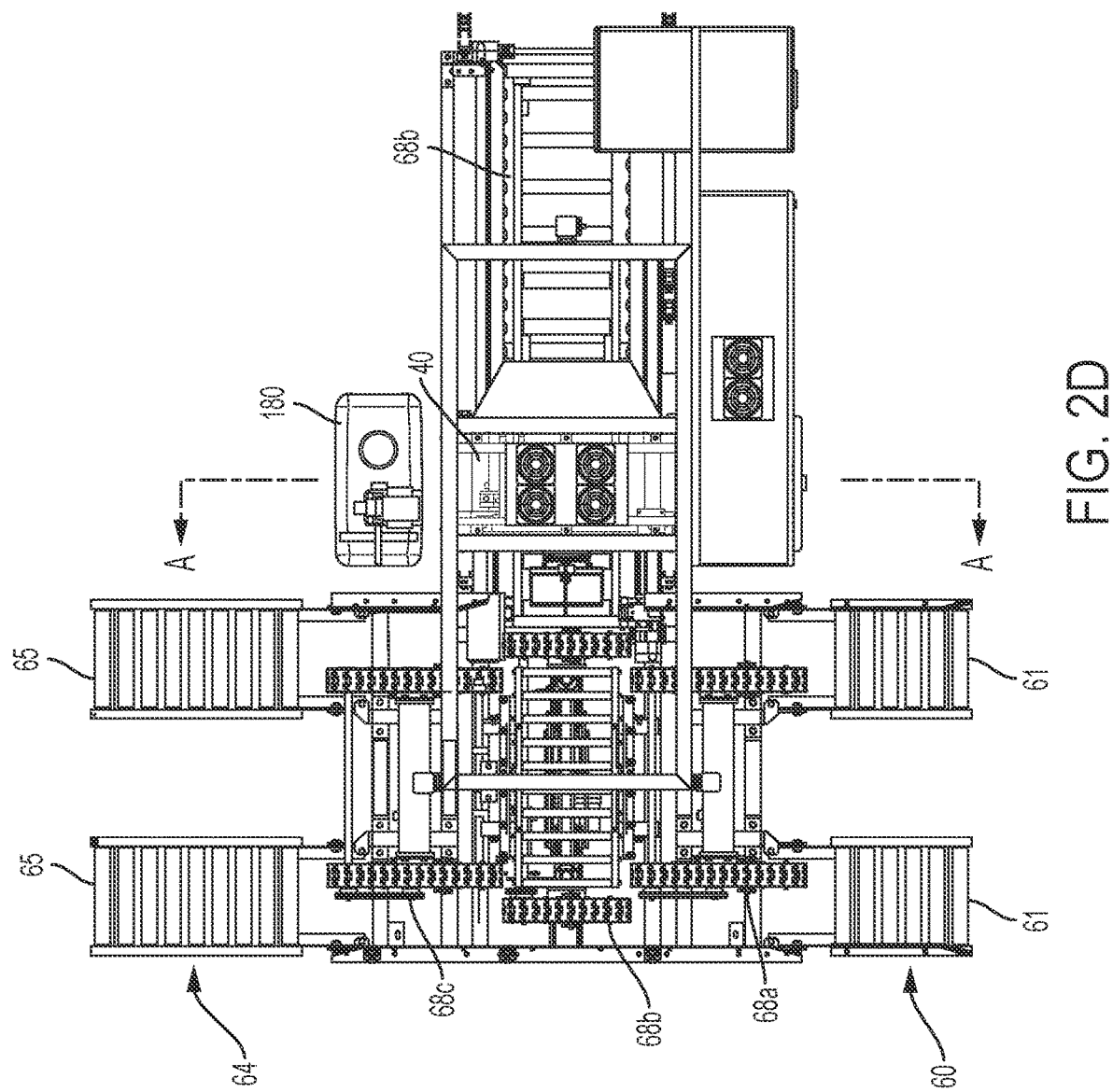
FIG. 2D is a front elevational view of the core analysis system of FIG. 2A.
Figure 2E:
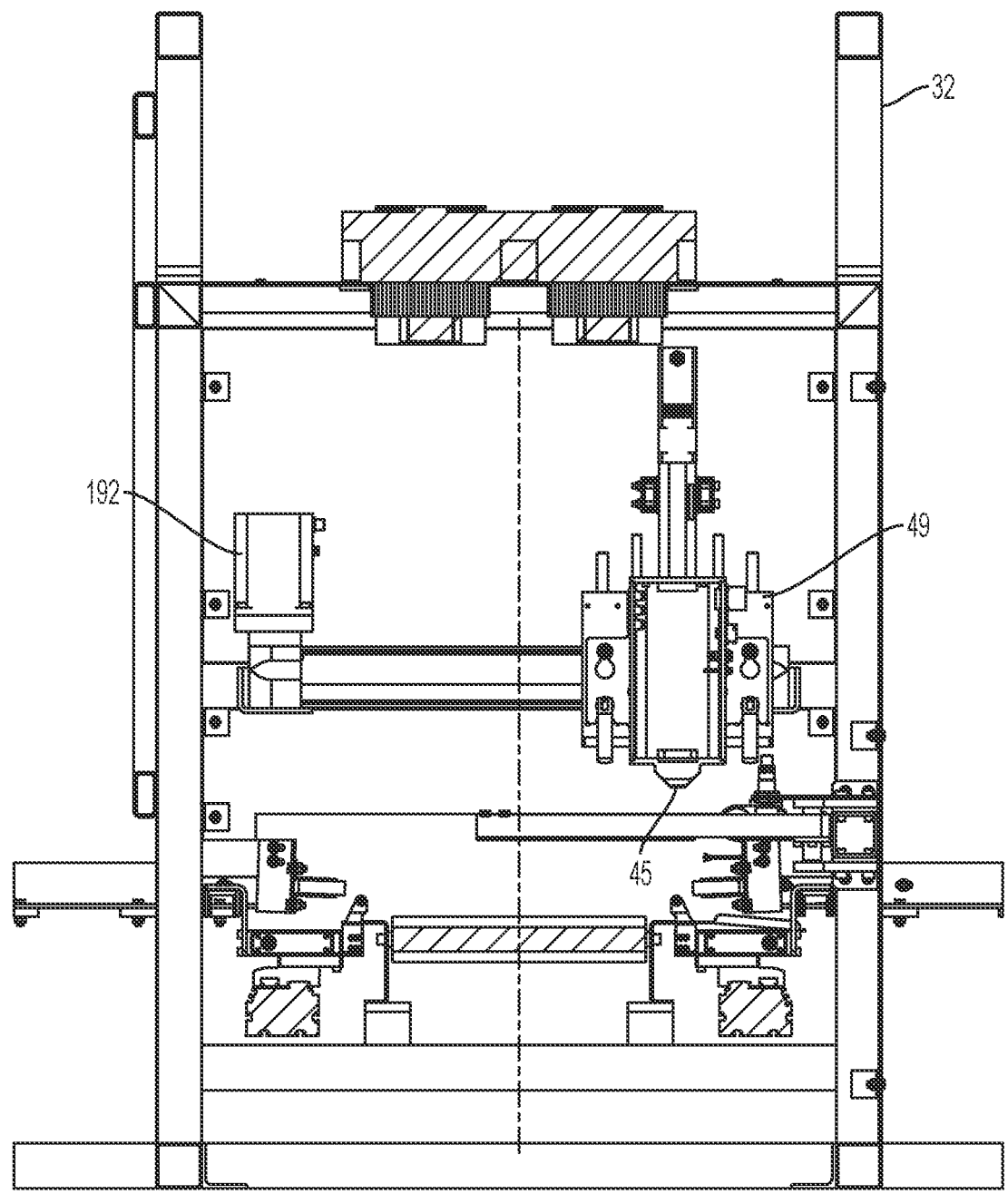
FIG. 2E is a cross-sectional view of the core analysis system of FIG. 2A, taken at line A-A depicted in FIG. 2D.

In exemplary aspects, and with reference to FIGS. 1A-2E, 4 and 4, the conveyor subassembly 50 can comprise input and output sections 58, 62. Optionally, in these aspects, the input and output sections 58, 62 can comprise respective roller assemblies 60, 64, which can be positioned in communication with respective intermediate conveyor sections as further disclosed herein. It is contemplated that each of the roller assemblies 60, 64 can be configured to receive a single container 90 (e.g., a single core box) or an adapter 440 as further disclosed herein. Optionally, in exemplary aspects, the roller assemblies 60, 64 can have operative widths that are at least slightly greater than the longitudinal lengths of the containers 90 (e.g., core boxes). In some aspects, as shown in FIGS. 1A-1C, the roller assemblies 60, 64 can each have a single roller that defines the entire width of the roller assembly. Alternatively, in other aspects, as shown in FIGS. 2A-2D, the roller assemblies 60, 64 can each have a pair of spaced roller arrays 61, 65 that cooperate to define the width of the roller assembly. In use, it can be advantageous to first and second spaced roller arrays 61, 65 positioned at the input and output sections of the conveyor subassembly 50. For example, it is contemplated that the use of two spaced roller assemblies 61 can reduce the total weight of the system (compared to a single continuous roller assembly of the same width). It is further contemplated that the use of two spaced roller assemblies can reduce the chance of breaking or disengagement of the pins used to hold the roller assemblies in a transport (e.g., folded) position.

Optionally, it is contemplated that the input section 58 can define the sample loading location. Optionally, it is contemplated that the output section 62 can define the sample unloading location. In additional aspects, the conveyor subassembly 50 can further comprise a plurality of intermediate sections 66 positioned between the input and output sections 58, 62. In further aspects, the conveyor subassembly 50 can further comprise a drive mechanism 70 configured to power movement of the intermediate sections. In exemplary aspects, each intermediate section 66 can comprise at least one actuator and a plurality of rollers, one or more conveyor belts, or combinations thereof.

In exemplary aspects, it is contemplated that the drive mechanism 70 can comprise a plurality of actuators that are operatively coupled to portions or sections of the conveyor subassembly 50 to selectively control movement of core samples and their containers relative to a plurality of axes. Optionally, it is contemplated that the drive mechanism 70 can be configured to control movement of the core samples and containers relative to the first and second axes 52, 54 and a vertical axis as further disclosed herein. In exemplary aspects, and with reference to FIG. 6B, the plurality of actuators can comprise at least one actuator 72a that is configured to effect movement of the core container relative to the first axis 52, at least one actuator 72b that is configured to effect movement of the core container relative to the second axis 54, and at least one actuator 72c that is configured to effect movement of the core container relative to a vertical axis that is perpendicular or substantially perpendicular to the first and second axes 52, 54. In further exemplary aspects, the actuators of the drive mechanism 70 can comprise linear actuators, such as for example and without limitation, electrical actuators, mechanical actuators, electro-mechanical actuators, hydraulic actuators, pneumatic actuators, and combinations thereof. However, depending upon the arrangement of each conveyor section, it is contemplated that the drive mechanism 70 can further comprise at least one rotational actuator.

In further exemplary aspects, as further disclosed herein and depicted in FIGS. 1-2D and 4, the plurality of intermediate sections 66 can comprise at least one intermediate section 68a, 68c configured to advance the one or more core samples relative to the first axis 52 and at least one intermediate section 68b configured to advance the one or more core samples relative to the second axis 54. In these aspects, and as shown in FIGS. 1A-2D, the first intermediate section 68a can comprise at least one conveyor belt that is operatively coupled to an actuator 72a to permit selective movement of a core sample relative to the first axis. In these aspects, it is contemplated that the first intermediate section 68a of the conveyor assembly can be configured to deliver the core box (containing the core sample) to the second intermediate section 68b of the conveyor assembly. Upon delivery of the core box to the second intermediate section 68b, an actuator 72c can selectively raise and lower the core box to permit engagement or coupling between the core box and at least one linear actuator 72b as disclosed herein. Upon coupling between the core box and the linear actuator 72b, the linear actuator can be configured to effect axial movement of the core box relative to the second axis 54, with the core box being supported by rollers positioned within the intermediate conveyor section 68b. In exemplary aspects, and with reference to FIG. 4, the intermediate conveyor section 68b can extend through the sample analysis area 42, and the linear actuator 72b can move the core box about and between three distinct locations along the second axis 54, including an initial position (labeled "3" in FIG. 4) before the core box is delivered to the analysis area, an intermediate imaging position on an opposing side of the XRF assembly (after the core box passes through the XRF assembly, labeled "4" in FIG. 4), and an analysis position (within the XRF assembly, labeled "5" in FIG. 4). Although disclosed herein as comprising at least one linear actuator 72b, it is contemplated that the intermediate conveyor section 68b can comprise, in addition or alternatively, a plurality of vertically oriented rollers that engage edge portions of the core box (or adapter as disclosed herein) and are driven by one or more rotational actuators to effect movement of the core box along the second axis 54. After the imaging/analysis process within the XRF assembly is completed, the actuator 72b can return the core box to its initial position (labeled "3"). It is contemplated that the intermediate conveyor section 68b can further comprise at least one linear actuator 72a that is coupled to at least one conveyor belt and configured to advance the core box to the third intermediate conveyor section 68c, which in turn, can have at least one linear actuator 72a that is coupled to at least one conveyor belt and configured to effect movement of the core box to the output roller assembly. In exemplary aspects, as shown in FIGS. 2A-2B, the conveyor belts of the first and third conveyor sections 68a, 68c can be staggered relative to the conveyor belts of the second conveyor section 68b.

Optionally, in exemplary aspects, the conveyor assembly can further comprise a stop plate that is positioned at a distal end of the output section (e.g., roller assembly 64). In these aspects, the stop plate can extend across at least a portion of the operative width of the output section to prevent the containers 90 (e.g., core boxes) from advancing beyond the distal end of the output section and falling from the conveyor assembly. In further exemplary aspects, it is contemplated that the core analysis system 10 can comprise a sensor configured to detect the presence of a container (e.g., core box) within the output section. In these aspects, it is contemplated that box sensor can be a conventional proximity sensor or encoder as is known in the art. In further aspects, it is contemplated that the box sensor can be communicatively coupled to the processor 80, and the processor can be configured to selectively control activation or stopping of the drive mechanism 70 of the conveyor assembly.

In operation, the drive mechanism 70 can drive axial movement of a first container (core box) from the input section (e.g., roller conveyor 60) onto a first intermediate conveyor section 68a (e.g., roller). As further disclosed herein, after the first container (core box) is positioned on the first intermediate conveyor section 68a (e.g., roller), it is contemplated that the input imaging assembly 100 (e.g., camera assembly) can be activated to identify the core samples within the first container and permit setup of the system parameters. In exemplary aspects, the drive mechanism 70 can drive movement of the container from the first intermediate conveyor section 68a (e.g., roller) to the second intermediate conveyor section 68b. Optionally, it is contemplated that the drive mechanism 70 can comprise a lifting actuator (or other lifting mechanism) that is configured to pull the container upwardly from the first intermediate conveyor section 68a to place the container in a staging position in which the container can be clamped or otherwise coupled to at least one actuator of the drive mechanism 70 that is configured to effect axial movement of the container relative to the second axis 54 to control entry and positioning of the container within the sample analysis area 42. As further disclosed herein, it is contemplated that the drive mechanism can comprise additional actuators that are configured to move the container relative to at least one of the first axis 52 and a vertical axis. In further aspects, after completion of the XRF scanning process, the drive assembly 70 can be operated to return the container to the initial position on the second intermediate conveyor section 68b. In another exemplary aspect, the third intermediate conveyor section 68c can be powered by the drive assembly to pull the container from the second intermediate conveyor section 68b through the wetting assembly and into a desired position under imaging assembly 130 to permit wet imaging of the core samples. After the wet image is captured, the powered belt conveyor at the third intermediate conveyor section 68c can be configured to push the container onto the output section (e.g., roller conveyor 64), where the container can optionally rest against a stop plate as further disclosed herein until it is removed by a system operator.

In exemplary aspects, and with reference to FIGS. 10A-12B, the system 10 can further comprise a tray adapter assembly 400. In these aspects, the tray adapter assembly 400 can allow the system to be compatible with different types and sizes of containers (e.g., different types and sizes of plastic core trays). The adapter assembly 400 can comprise an adapter 440 comprising a steel plate having inwardly folded longitudinal and transverse walls 442, 444 and defining at least one alignment opening 446 extending through the thickness of the plate. Optionally, the adapter 440 can comprise at least two openings that are positioned proximate opposing corners of one end of the plate. In use, it is contemplated that the adapter 440 can be used with any core container (e.g., core tray) that is compatible with the disclosed system, with the folded edges allowing different trays to fit and convey within the system. It is contemplated that actuator and data acquisition controls on each respective type of core box can be controlled and set by the methods engineer through use of the software or databases disclosed herein.

In use, the adapter 440 can be positioned at the input section 58 (e.g., the roller assembly 60) of the conveyor subassembly, and the core box can be positioned on the adapter, with the longitudinal and transverse edges of the adapter surrounding the core box. Due to the folded construction of the longitudinal and transverse edges, it is contemplated that the edges can be biased toward a center portion of the adapter such that, in a resting position (before receipt of core box), the edges define a minimum diameter of the adapter. Upon receipt of a core box, the edges can be configured to deform in an outer direction as necessary to accommodate the operative dimensions of the core box. In exemplary aspects, when the adapter is positioned at the input section 58, it is contemplated that the longitudinal edges of the adapter can be oriented perpendicular or substantially perpendicular to the first axis 52 (and parallel or substantially parallel to the second axis 54). This general orientation can be maintained as the adapter is advanced along the first axis by the drive mechanism 70 as disclosed herein.

Figure 10A:
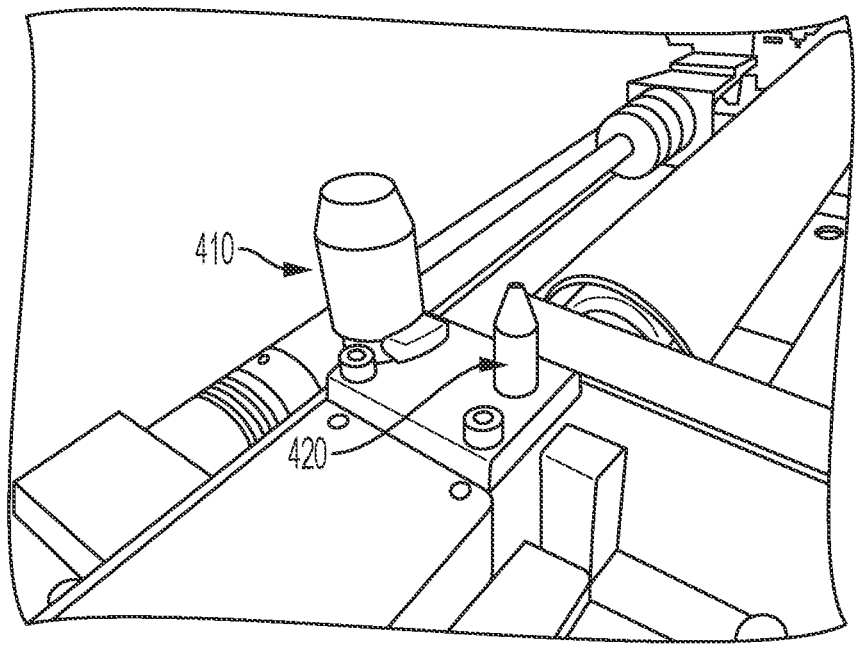
FIG. 10A is an image depicting a stop projection and a locator pin of an exemplary tray adapter assembly as disclosed herein.
Figure 10B:
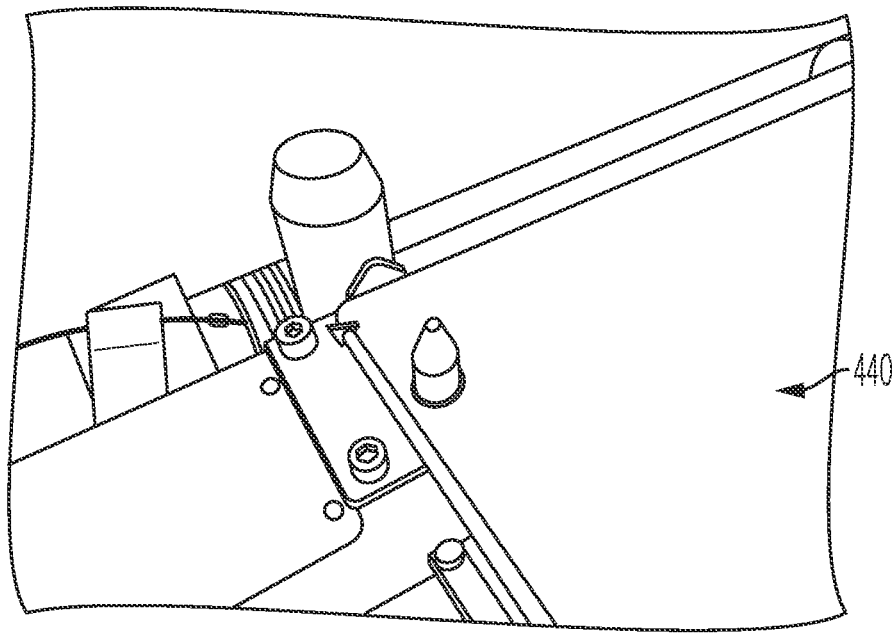
FIG. 10B is an image depicting the placement of an adapter relative to the stop projection and the locator pin such that the locator pin extends through an alignment opening of the adapter.
Figure 11A:
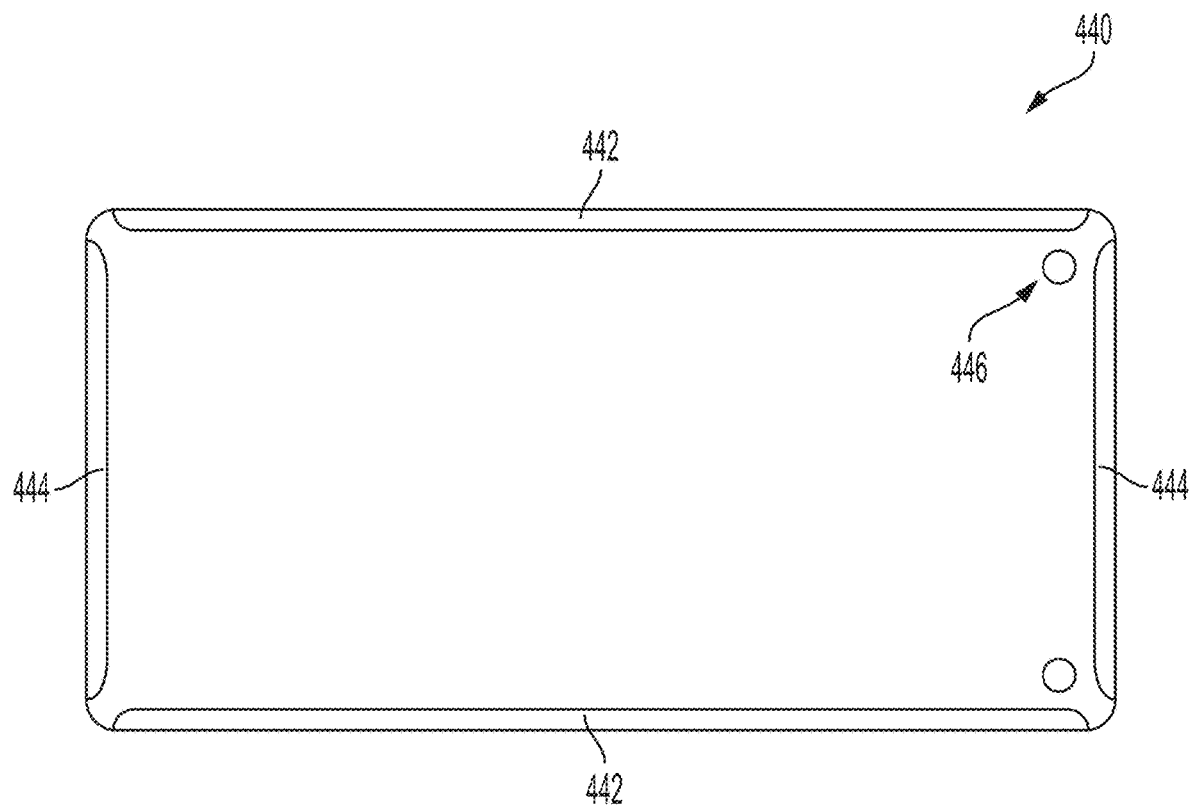
FIG. 11A is a top plan view of an exemplary adapter as disclosed herein.
Figure 11B:
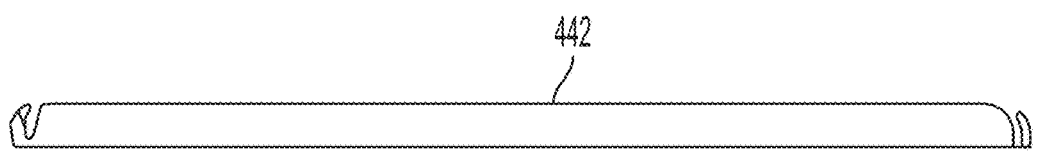
FIG. 11B is a side elevational view of a longitudinal edge of the adapter of FIG. 11A.
Figure 11C:
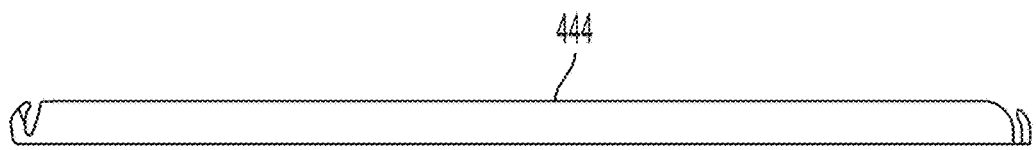
FIG. 11C is a side elevational view of a transverse edge of the adapter of FIG. 11A. As shown, each edge of the adapter can be folded inwardly toward an interior portion of the adapter.
Figure 12A:
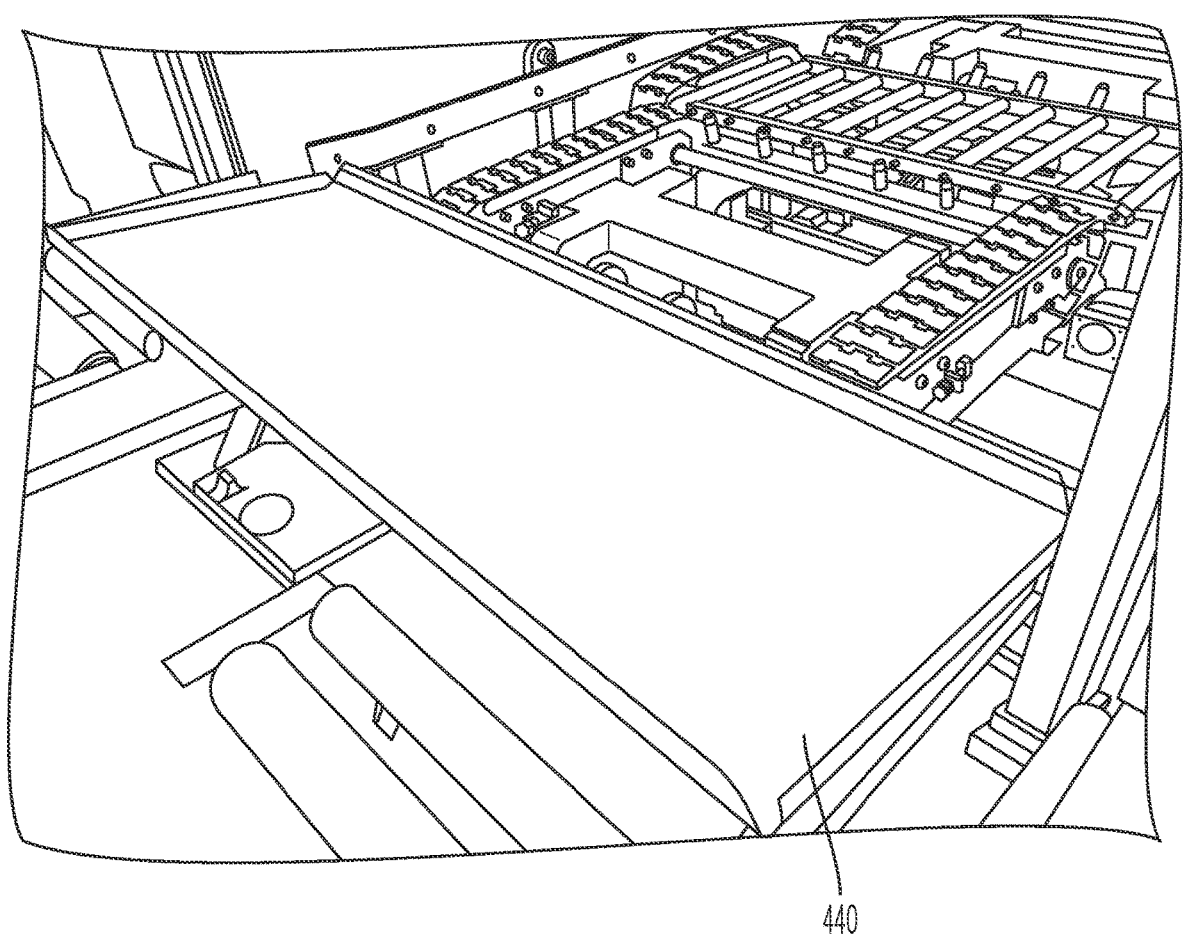
FIG. 12A is an image depicting an exemplary adapter extending across two spaced input rollers as further disclosed herein.
Figure 12B:
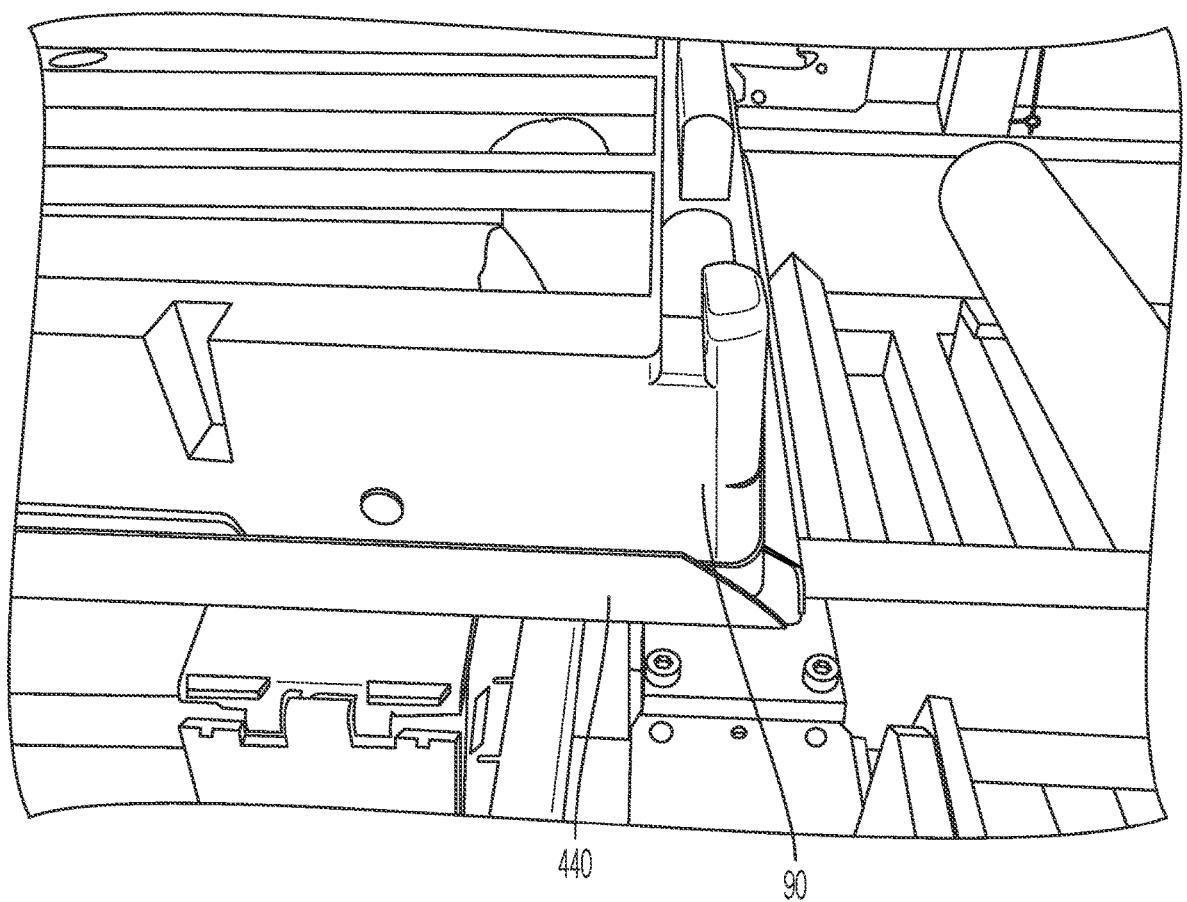
FIG. 12B is an image depicting a container (e.g., core tray) positioned within an exemplary adapter as disclosed herein.
Figure 13A:
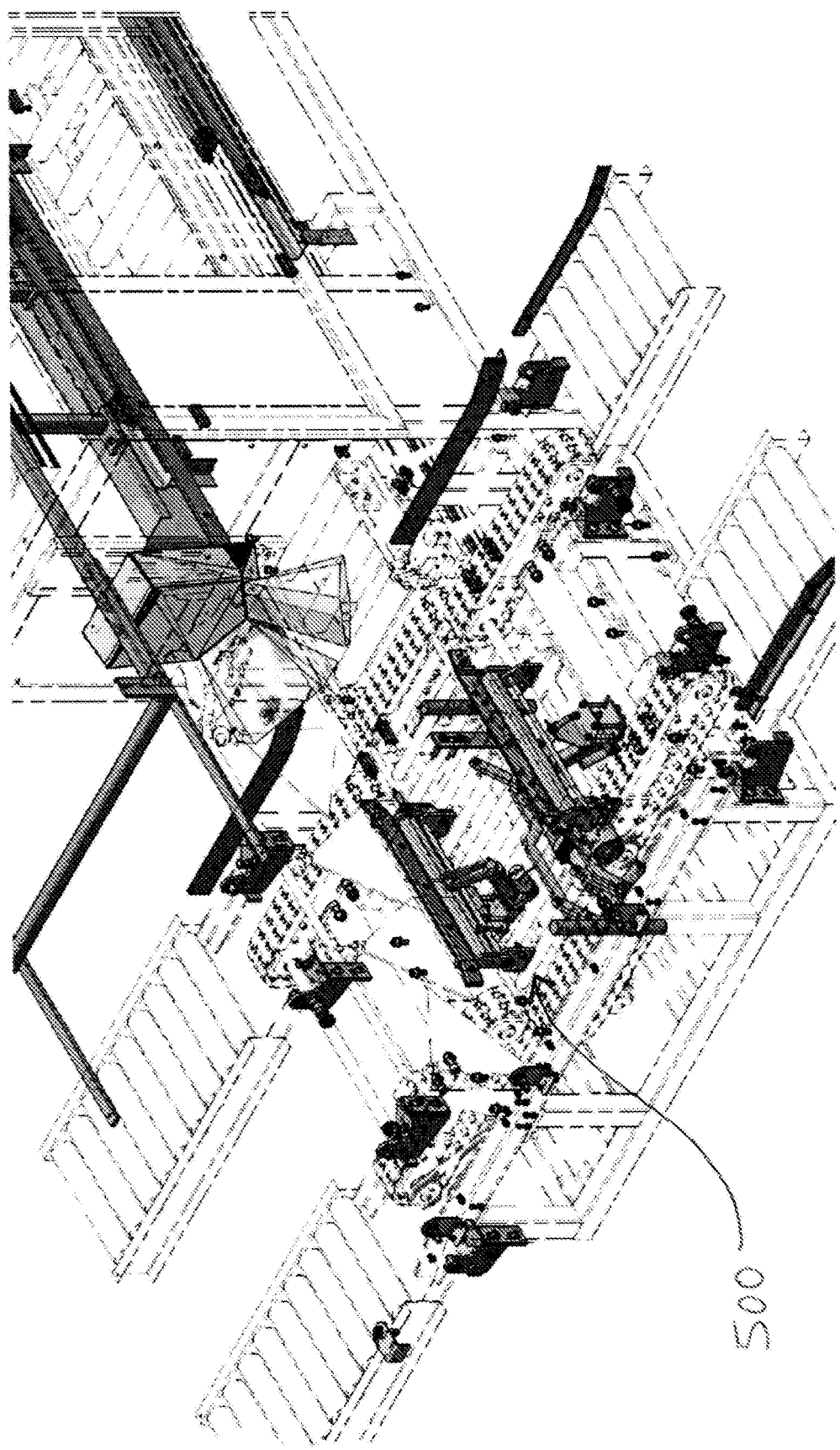
FIG. 13A is a perspective view of an exemplary analysis assembly having a tray centering subassembly as disclosed herein.
Figure 13B:
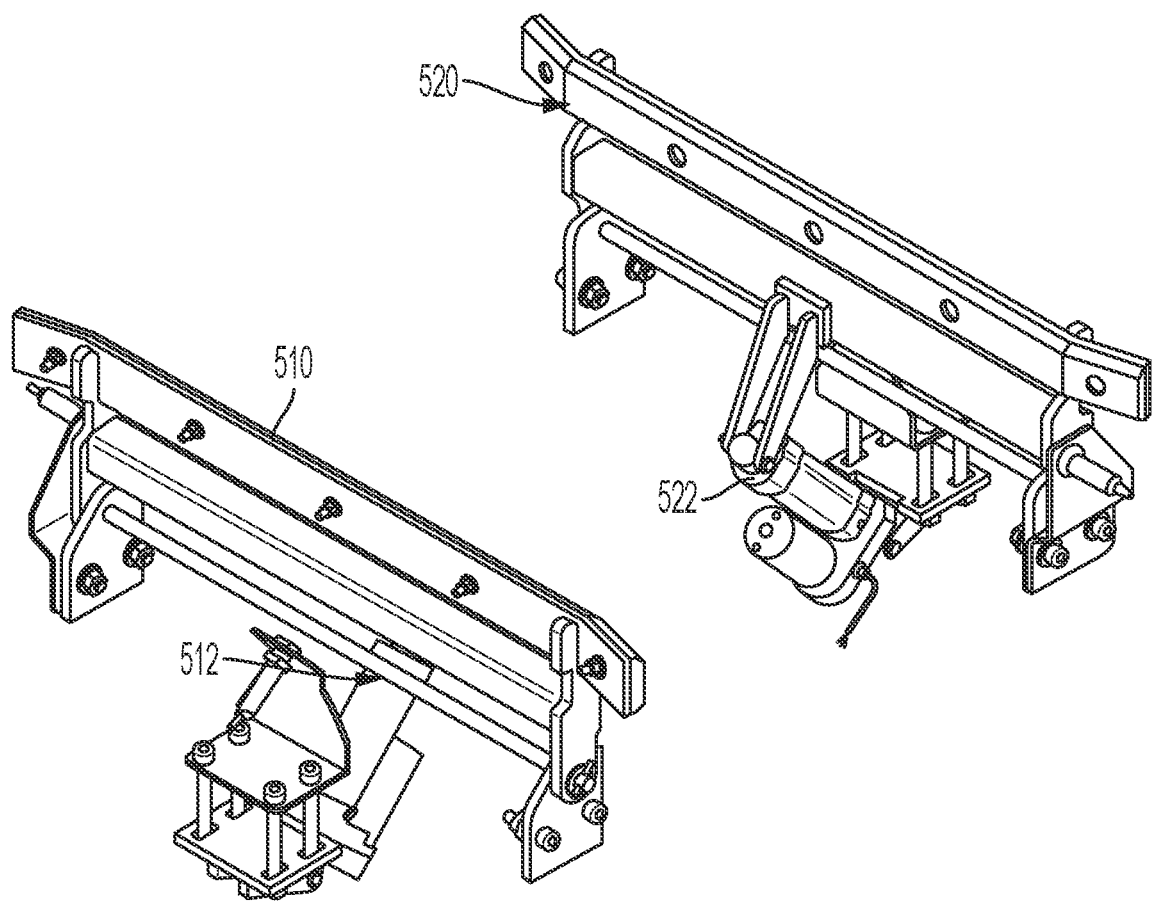
FIG. 13B is a perspective view of the tray centering subassembly of FIG. 13A. As shown, the tray centering subassembly can comprise first and second guides that are activated by respective actuators.
Figure 14C:
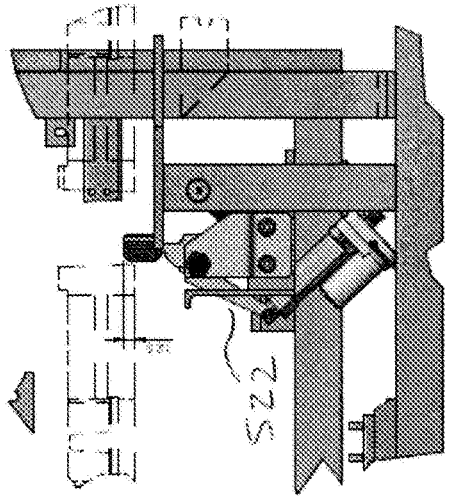
FIGS. 14A-14C show the progression of movement of a guide of the tray centering subassembly as a core tray (shown in phantom line) approaches the tray centering subassembly. More particularly.
Figure 14B:
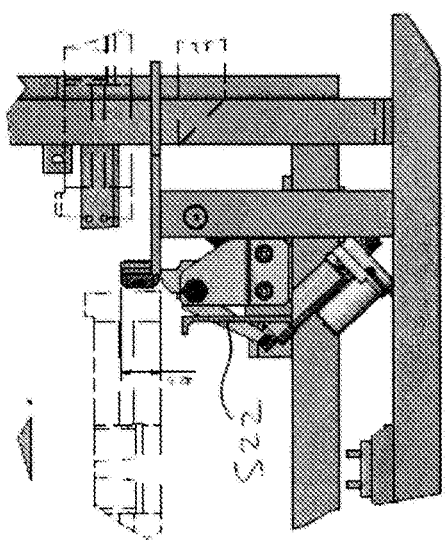
Figure 14A:
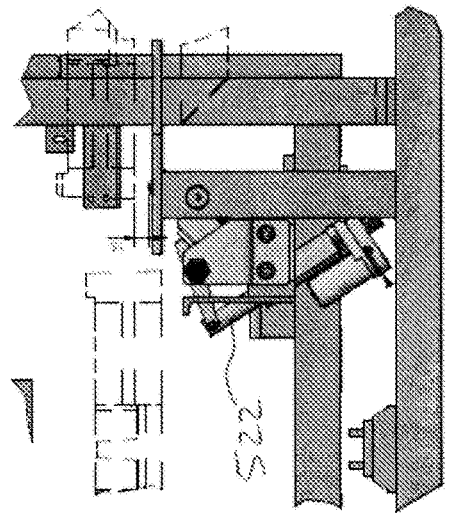

As shown in FIGS. 10A-10B, the tray adapter assembly 400 can further comprise at least one stop projection 410 and at least one locator pin 420 that are secured to, coupled to, or integrally formed with a linear actuator 72b that is configured to effect movement of the adapter 440 (and the core tray on the adapter) relative to the second axis 54 as disclosed herein. In use, the locator pin 420 can be received within and through an alignment opening of the adapter 440 when the adapter (and the core tray) is received by the second intermediate conveyor section 68b. In these aspects, the lift actuator 72c can selectively raise and then lower the adapter 440 such that the locator pin 420 passes through and projects upwardly relative to a corresponding alignment opening 446, and a corner portion of the adapter 440 is positioned between the locator pin and the stop projection 410 to thereby secure the adapter in place. Optionally, in exemplary aspects, the tray adapter assembly 400 can comprise first and second stop projections 410 and first and second locator pins 420, with the first pin being received through a first opening of the adapter and the second pin being received through a second opening of the adapter positioned on an opposing side of the adapter relative to the first axis 52. In further aspects, the adapter assembly can further comprise a proximity sensor 430 that is configured to detect placement of the adapter tray over the locator pin 420 such that the adapter is securely engaged by the locator pin and the stop projection 410. After the processor 80 receives confirmation of proper positioning of the adapter 440 from the proximity sensor 430, the system can proceed with advancement of the adapter 440 (and the core box 90) relative to the second axis as further disclosed herein, and further processing can proceed as further disclosed herein.

In further exemplary aspects, and with reference to FIGS. 13A-14C, the system 10 can comprise a tray centering assembly 500 that can be positioned to cooperate with the second intermediate conveyor section 68b, which as further disclosed herein, can comprise a lifting table for permitting vertical movement of an adapter and core box. In use, the tray centering assembly 500 can ensure that the adapter 440 (and the core boxes on the adapter) is consistently and precisely oriented relative to the second axis 54. It is further contemplated that the centering of the adapter 440 can help ensure alignment between the locator pins 420 of the adapter assembly 400 and the alignment openings 446 of the adapter 440. In exemplary aspects, the tray centering assembly 500 can comprise first and second guides 510, 520 that are positioned on opposing sides of the intermediate conveyor section 68b relative to the first axis 52. Each guide 510, 520 can be operatively coupled to a respective actuator 512, 522 that is configured to pivot the guide from a lowered, disengaged position to a raised, engaged position (to contact the longitudinal edges of the adapter (and/or portions of the core box) and adjust the orientation of the adapter and core box as needed to continue further processing. It is contemplated that, in response to a signal from the processor 80 that the adapter (and core box) is being lowered, the actuators 512, 522 can be configured to effect movement of the guides from the lowered position to the raised position. Upon engagement between the guides and the adapter, the adapter and the core box can be properly aligned relative to the second axis 54, and thereby prevent undesired contact or alignment defects and make the system more robust, reliable, and repeatable. After proper alignment of the adapter and core box are established, the actuator 72c, using the lifting table, can raise the adapter to an operative height at which the adapter can be axially advanced relative to the second axis 54. It is contemplated that the guides can be positioned sufficiently below the raised position of the adapter such that the guides do not interfere with movement of the adapter and core box relative to the second axis 54. In use, it is contemplated that the centering process can be performed in an automated fashion as part of the typical lowering process for the adapter and core box. In exemplary aspects, this automation can be driven by the PLC 80b disclosed herein.

Figure 3:
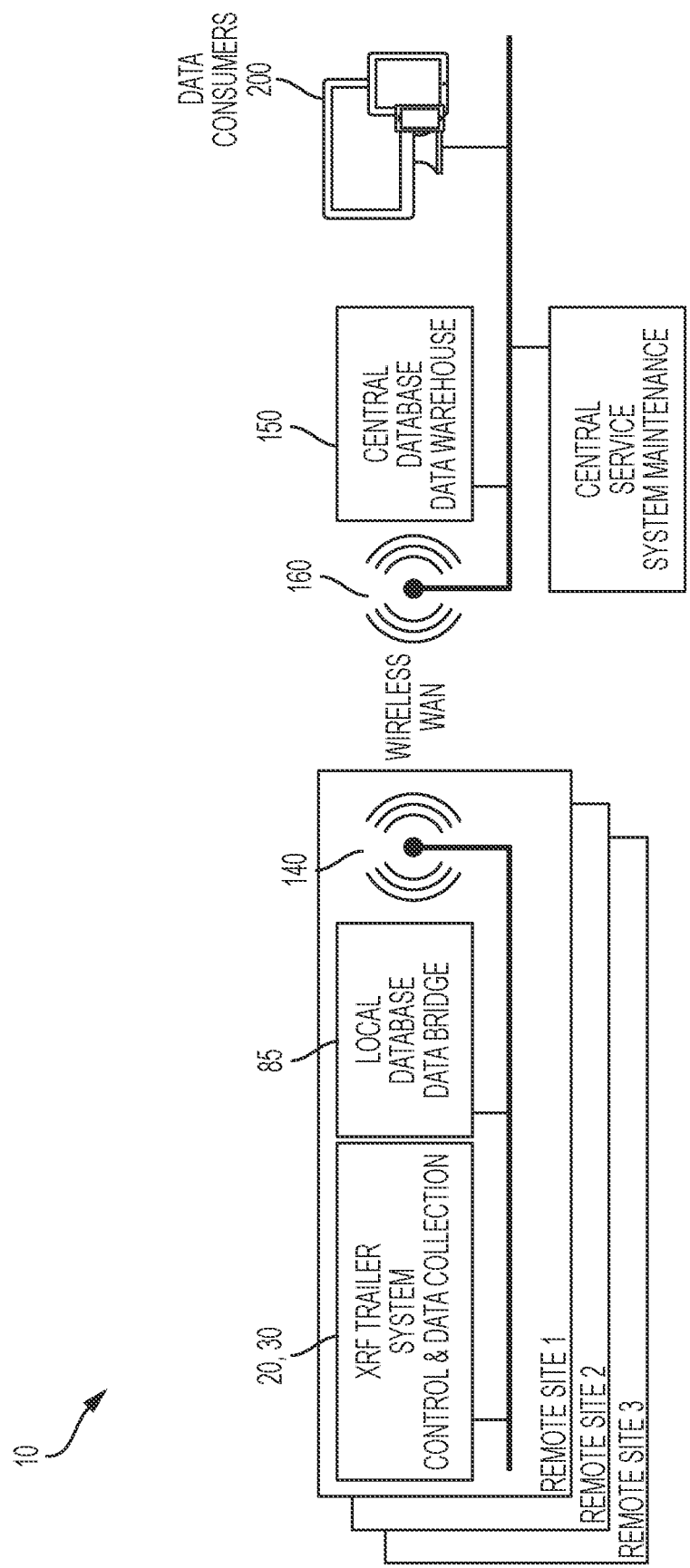
FIG. 3 is a schematic diagram depicting electrical communication between a sample analysis assembly, a central database, and consumers as disclosed herein.

In still further exemplary aspects, and with reference to FIGS. 3-6A, the core analysis system 10 can further comprise a first wireless transmitter-receiver 140 communicatively coupled to the processor 80. In still further exemplary aspects, the core analysis system 10 can further comprise a database 150. In still further exemplary aspects, the core analysis system 10 can further comprise a second wireless transmitter-receiver 160 communicatively coupled to the database 150. In these aspects, it is contemplated that the second wireless transmitter-receiver 160 can be configured to receive information from the first wireless transmitter-receiver 140 and to transmit information from the database 150 to the first wireless transmitter-receiver 140. Optionally, in exemplary aspects and as shown in FIG. 3, it is contemplated that the database can be selectively remotely accessible to consumers 200.

In still further exemplary aspects, and with reference to FIGS. 1-2D and 4, the core analysis system 10 can further comprise a user interface 170. In these aspects, it is contemplated that the processor 80 can be communicatively coupled to the user interface 170 and configured to receive one or more inputs from the user interface. It is further contemplated that the user interface 170 can comprise a display that is configured to present information to a system user related to the core sample analysis and the performance of the system. In exemplary aspects, the user interface 170 can comprise a single human-machine interface that is installed on an outer portion of the trailer. In these aspects, it is contemplated that the user interface 170 can be shaped such that it can be protected by a cover during transport operations. It is further contemplated that the user interface 170 can be weather-resistant such that it can be used in a variety of weather conditions. In exemplary aspects, the user interface 170 can be touchscreen-enabled and natively support a desired screen resolution (e.g., 1280×1024 resolution with 4:3 Aspect ratio). In these aspects, it is contemplated that the user interface 170 can comprise a display that permits data input and display via textual references and drop down lists rather than input of coded values to make for a more user-friendly interface. Optionally, it is further contemplated that the user interface 170 can provide point-and-click options and/or automated data entry to minimize typing and/or keyboard entry.

In exemplary aspects, it is contemplated that the user interface 170 can be provided as a component of a computer workstation. However, in other aspects, it is contemplated that the user interface 170 can be provided as a portion of a remote computing device, such as a smartphone, tablet, personal data assistant (PDA), or laptop computer.

In further exemplary aspects, and with reference to FIG. 4, it is contemplated that the core analysis system 10 can comprise a power source 184 that is configured to supply electrical power to other components of the system. Optionally, in these aspects, the power source 184 can comprise a landline electrical supply, an on-board generator, and a battery-backed uninterruptable power supply (UPS). In these aspects, it is contemplated that the electrical supply can accept a commercial electric supply while providing load-side circuit protection. It is further contemplated that the electrical supply can transform a commercial electrical input (e.g., 230 V at 50 Hz) into a desired output (e.g., 24 VDC at 160 Amps) with appropriate load-side circuit protection. It is contemplated that the on-board generator can have a local generator control panel that enables starting, control, and operation of the generator. Optionally, the generator can include a monitoring device that is configured to produce an alarm or an output signal that indicates the generator has stopped working or is not functioning correctly. It is contemplated that the battery-backed uninterruptable power supply can supply power to the processing components of the system. In use, it is contemplated that power can be provided to the imaging and camera assemblies for a selected period of time (e.g., at least 30 minutes) before a shutdown command is signaled to their corresponding processing components. When the uninterruptable power supply is supplying power to the processing components, it is contemplated that the control functions of the processing components can be halted.

In further exemplary aspects, and with reference to FIG. 4, it is contemplated that the core analysis system 10 can comprise an HVAC unit 180 that is configured to maintain the temperature within the sample analysis area 42 at a desired level, as may be stipulated by manufacturers of the components of the XRF detection subassembly 40. Optionally, it is contemplated that the HVAC unit can be configured to maintain the temperature within the sample analysis area 42 at a temperature ranging from about 20° C. to about 24° C. under normal operating conditions. In exemplary aspects, it is contemplated that the HVAC unit can be powered from the domestic electrical supply to the trailer, which may be derived from a landline power source or an onboard generator as further disclosed herein. In use, it is contemplated that digital XRF imaging equipment can be sensitive to ambient temperature variation, and rapid changes in temperature and extremes of temperature can severely damage digital detectors. Accordingly, it is contemplated that temperature control within the sample analysis area 42 (particularly within the XRF sensor enclosure) is critical to obtaining accurate data and protecting the system components. In exemplary aspects, the core analysis system 10 can further comprise an environmental monitoring device that logs temperature variations within the sample analysis area 42 or, more particularly, within the XRF sensor enclosure.

In still further exemplary aspects, and with reference to FIG. 4, it is contemplated that the core analysis system 10 can comprise a gas (e.g., Helium) supply source 182 that is configured to supply gas to the XRF detection subassembly 40. Optionally, in these aspects, the gas supply source can be an onboard Helium supply subsystem that is configured to provide a dry helium cover gas to the XRF instrument (e.g., X-ray source). In use, it is contemplated that the processor 80 can be configured to selectively initiate and cease delivery of gas to the XRF instrument. Optionally, in exemplary aspects, the gas supply source 182 can comprise a 2-stage bottle regulator that reduces bottle pressure from above 2,000 psi to about 60 psi (+/−10 psi). In further aspects, the gas supply source 182 can optionally comprise a pressure switch on an outlet side of the bottle regulator that delivers a signal to the processor 80 when the pressure falls below a selected level, such as for example and without limitation, 50 psi. In still further aspects, it is contemplated that the core analysis system 10 can comprise an instrument regulator that is configured to reduce the pressure at the outlet side of the 2-stage regulator pressure to 15 psi (+/−5 psi). In still further exemplary aspects, the gas supply source 182 can comprise an instrument flow control device that enables flow from the outlet side of the instrument regulator to the XRF instrument. In these aspects, it is contemplated that the instrument flow control device can be communicatively coupled to the processor 80 such that the processor can selectively control a rate of gas flow between the outlet of the instrument regulator and the inlet of the XRF instrument. Optionally, it is contemplated that the rate of gas flow can range from about 0.0 Liters per minute (LPM) to about 1.0 LPM.

In use, the disclosed core analysis system can provide on-site analysis and data collection capabilities for drill core samples. Optionally, in exemplary aspects, it is contemplated that a plurality of core analysis systems can be operated in parallel from distinct locations, with respective data sets from each core analysis system delivered to a centralized server system for further analysis as disclosed herein.

In use, it is contemplated that the disclosed core analysis systems can reduce the costs associated with processing assays, including costs conventionally associated with sample preparation, sample transport, sample tracking, and data processing. It is further contemplated that the disclosed core analysis systems can provide improved data quality in comparison to existing core analysis systems. More particularly, it is contemplated that the disclosed core analysis systems can preserve heterogeneity and objectivity while also associating time and depth data with each core sample and providing systematic collection and linking of data sets. It is further contemplated that the disclosed core analysis systems can provide an increase in the speed of decisions by drilling system operators or remote customers. More particularly, it is contemplated that the disclosed core analysis systems can provide near real-time access to core data via a centralized database, which can be accessed by any networked computing device (optionally, computing devices, from multiple users or customers). In exemplary aspects, as further disclosed herein, the processor 80 can be configured to provide customizable threshold notifications associated with various core parameters to system users or customers.

In exemplary aspects, and with reference to FIGS. 4-6B, the processor 80 can comprise a processing assembly comprising a plurality of processing components. Optionally, in these aspects, the processor 80 can comprise at least one industrial process controller (IPC) 80*a* and at least one programmable logic controller (PLC) 80*b*. In exemplary aspects, the IPC can be an industrial grade computer, and the system operator can interface with the IPC through the user interface 170 disclosed herein. In exemplary aspects, it is contemplated that the IPC can be configured to perform a variety of functions, including one or more of the following: monitoring for loss of power and halting control functions when a power loss is detected; controlling system restart using operator confirmation after reestablishing power; signaling a shutdown command to an industrial data concentrator (IDC) when the UPS indicates backup power is exhausted; performing a shutdown when the UPS indicates backup power is exhausted; interfacing with the PLC by operating as a Modbus Master, which enables communication among many devices connected to the same network; monitoring activation of the PLC over industrial network communications (Modbus) to determine if communications are established and operating; halting control functions when a PLC communications loss is detected; processing logic to indicate activation or readiness of the IPC over industrial network communications (Modbus); reading/writing status data to one or more PLC Modbus Slave registers during cycle operations; interfacing with three (3)-axis motion controllers 80*c*, 80*d*, 80*e* (e.g., X-, Y-, and Z-axis controllers) of the conveyor assembly by operating as a Modbus Slave; monitoring a Modbus connection with each axis motion controller and halting control functions when a communications loss is detected; reading and writing values into an interface block used by Modbus that reads and writes from each Axis Motion Controller; interfacing with an operator through the user interface 170 to indicate status of the system; interfacing with an operator through the user interface 170 to collect and authenticate login credentials and set application privileges; interfacing with the operator through the user interface 170 to collect information required by the system during setup operations; interfacing with the XRF Instrument to query, configure, and command the unit during cycle operations; interfacing with the image files captured by the imaging assemblies during cycle operations; processing images to extract and parse OCR data from image files during cycle operations; interfacing with the central database to retrieve information required by the system during startup, setup, and cycle operations; interfacing with the memory 85 to store information collected by the system during startup, setup, and cycle operations; interfacing with the memory 85 to transfer information collected by the system during cycle operations to the IDC; interfacing with the memory 85 to perform database maintenance functions; and processing XRF data using calibration files stored in the memory 85.

In exemplary aspects, the PLC of the processor 80 can comprise an Allen-Bradley MicroLogix 1400 Small Programmable Logic Controller. Optionally, the PLC can be configured to provide input/output control to the core analysis system 10. In exemplary aspects, the PLC can comprise one or more of the following: 24 VDC inputs, relay outputs, an expansion PNP output chassis, a 10/100 EtherNet/IP Port, EtherNet/IP Messaging, DNP3 over IP, and Modbus TCP/IP as are known in the art. In further exemplary aspects, the PLC can operate as a Modbus Slave and host Bit and Word registers to support required interfaces with the Modbus Master (IPC). In further exemplary aspects, the PLC can comprise an axis control system that is configured to provide multi-axis (e.g., three-axis) control of the movement of the components of the core analysis system. In exemplary aspects, the axis control system can comprise three Festo CMMO-ST Motion controllers that are configured to provide axis control for a Trailer Core Scanner module as shown in FIG. 5.

Data Networks

Figure 5:
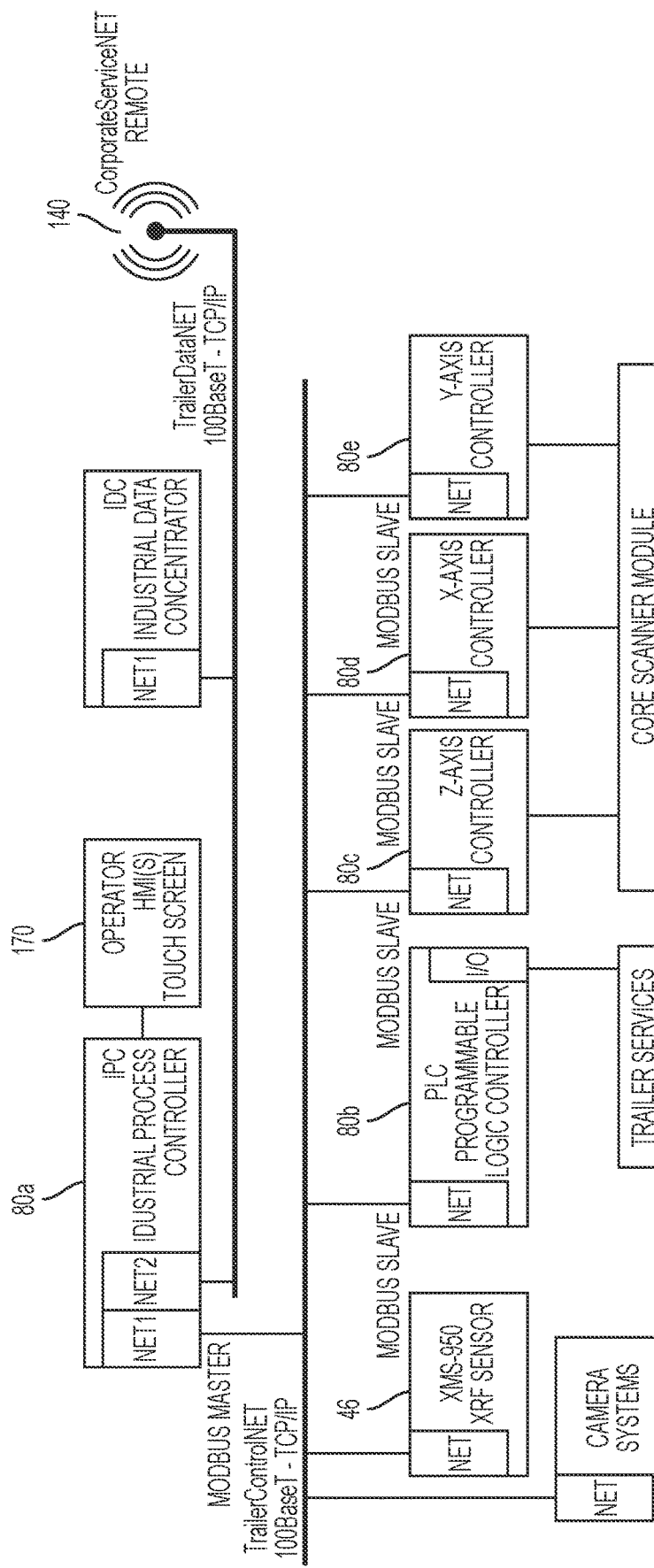
FIG. 5 is a schematic diagram depicting an exemplary data network arrangement for use with the core analysis system as disclosed herein.
Figure 6A:
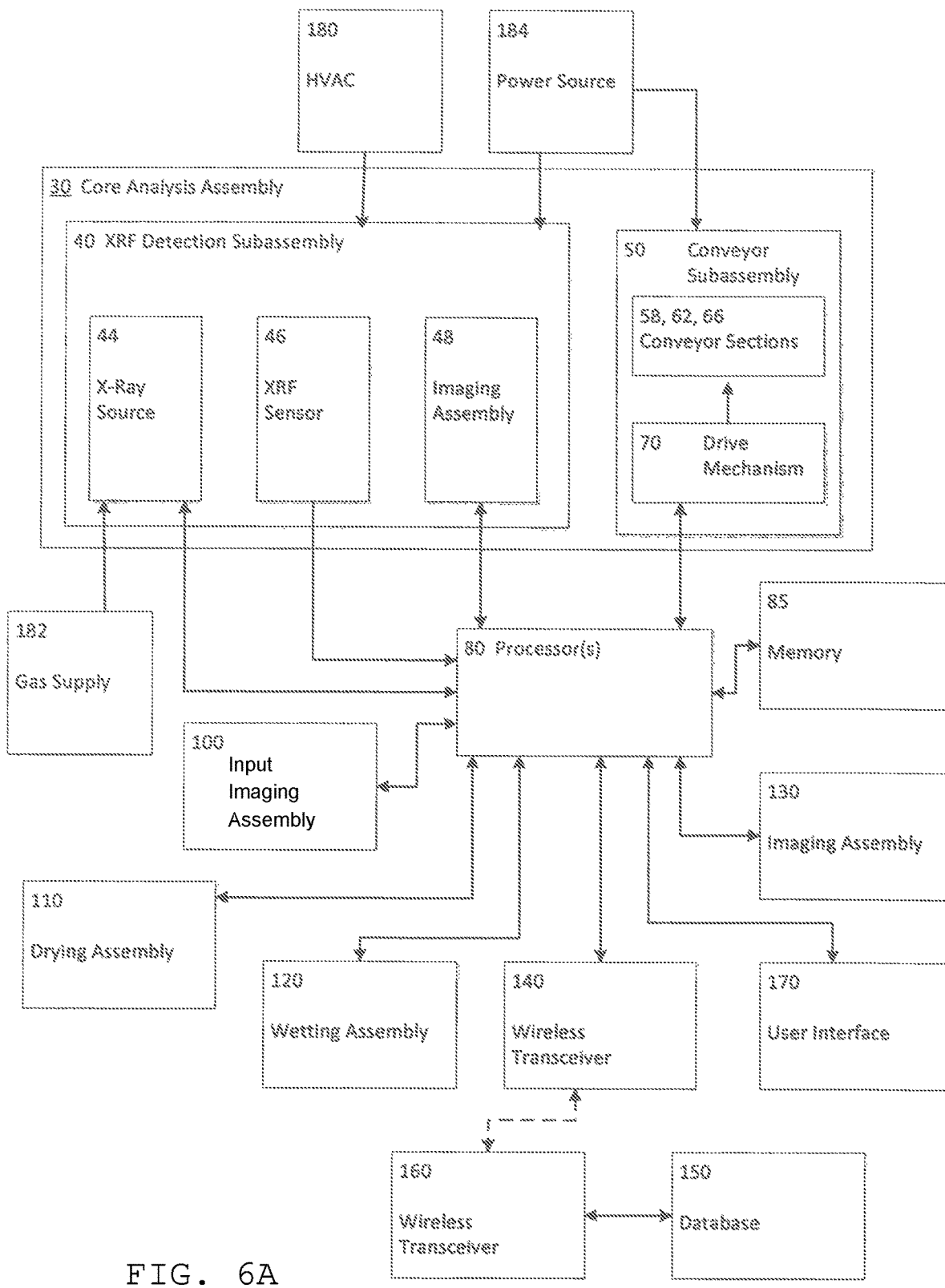
FIG. 6A is a schematic diagram depicting the communication between components of an exemplary core analysis system as disclosed herein.
Figure 6B:
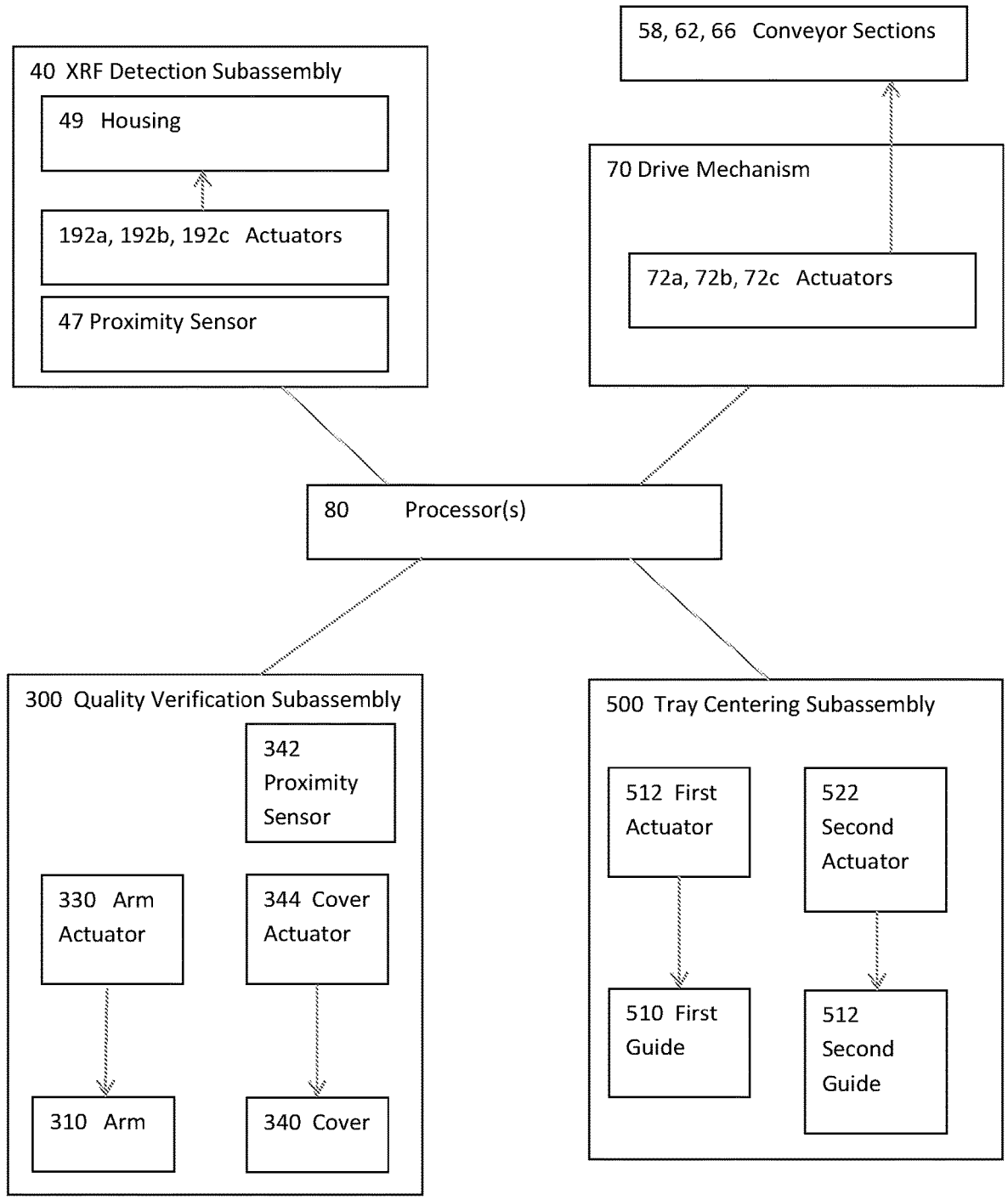
FIG. 6B is a schematic diagram depicting the communication between the processing components of an exemplary core analysis system and various actuators positioned throughout the system.
Figure 7A:
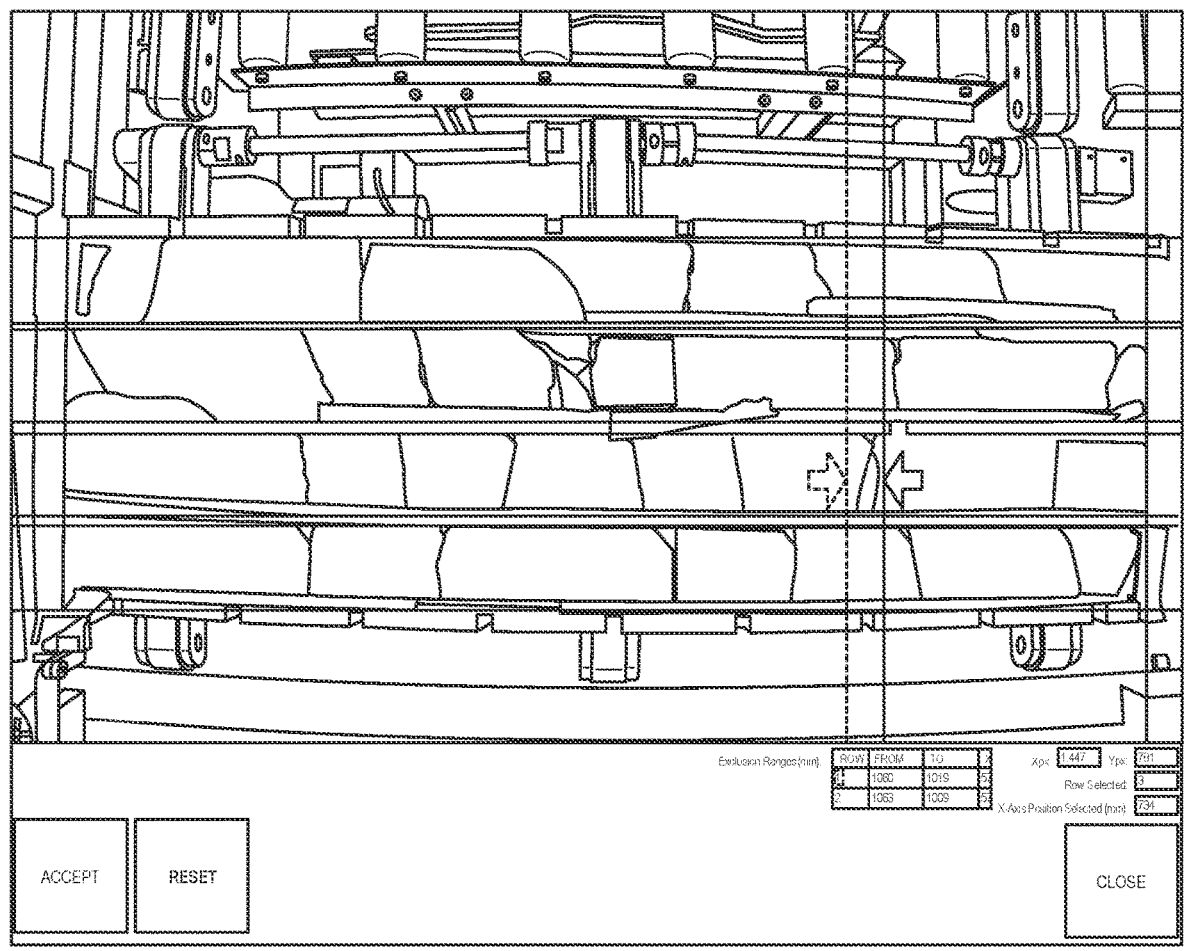
FIGS. 7A-7B are images of exemplary displays of core sample segments on a core box as disclosed herein. As shown, a system operator can use a human machine interface to select or "tag" portions of the core sample segments for exclusion from analysis as further disclosed herein.
Figure 7B:
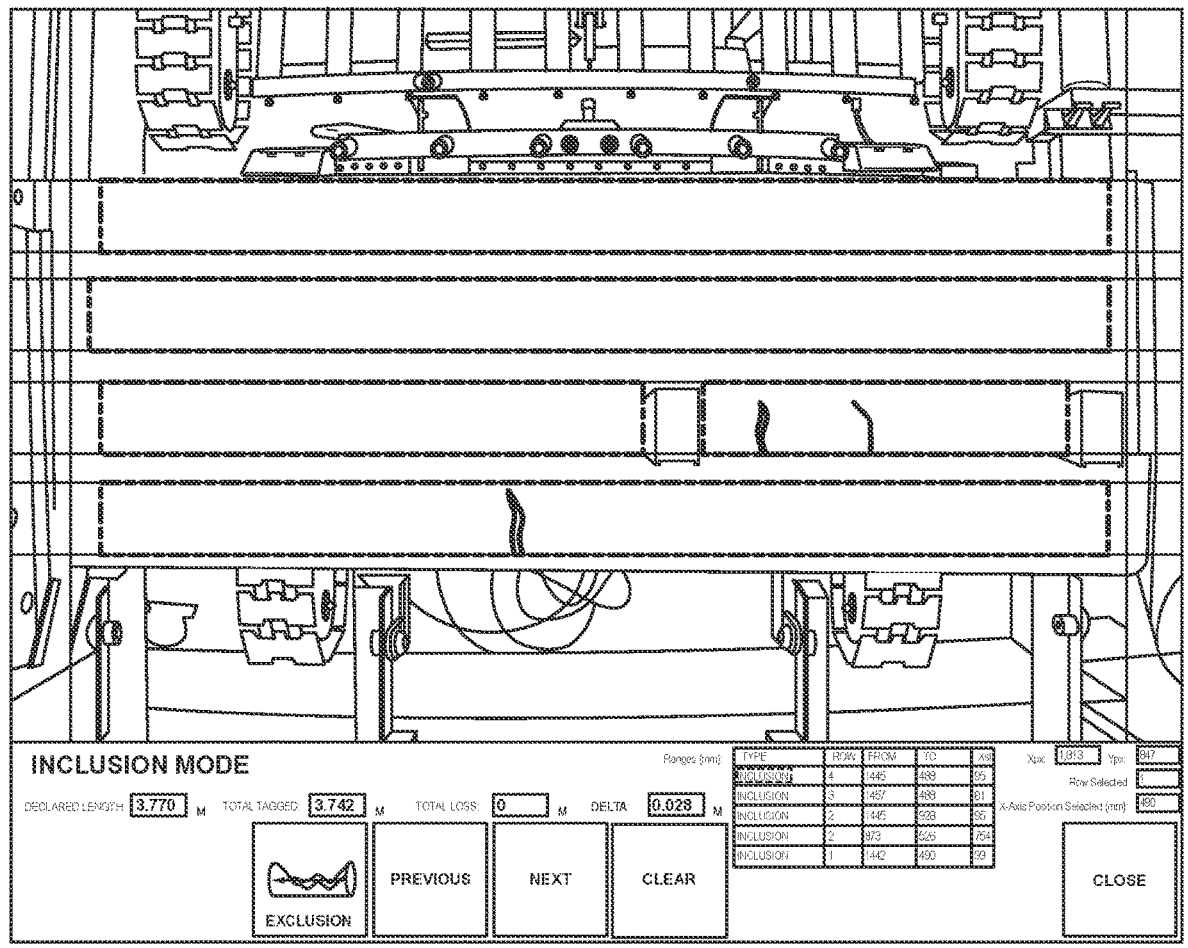
Figure 8A:
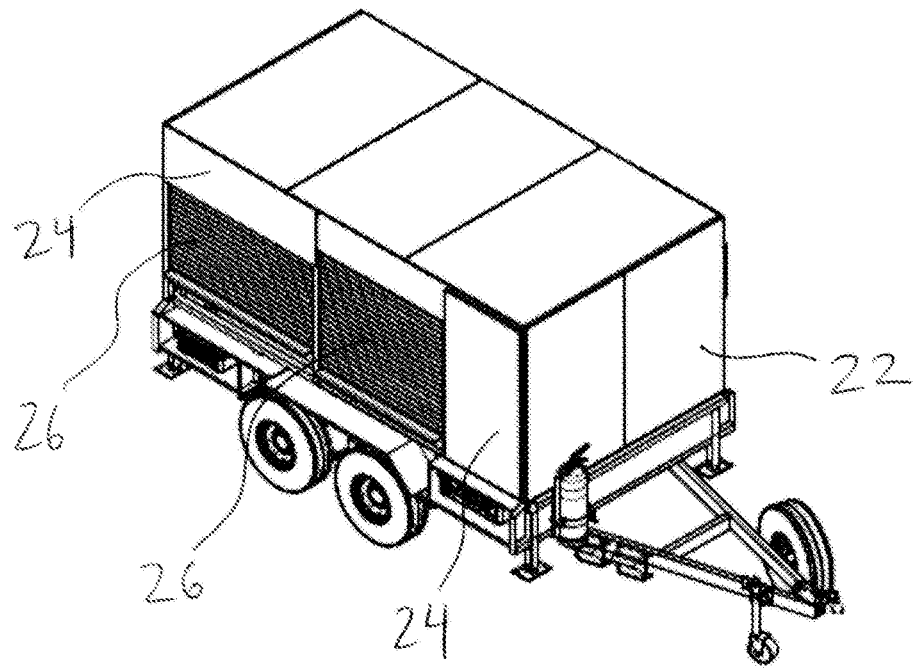
FIGS. 8A-8B are left and right perspective views of an exemplary trailer for enclosing and transporting an analysis assembly as disclosed herein.
Figure 8B:
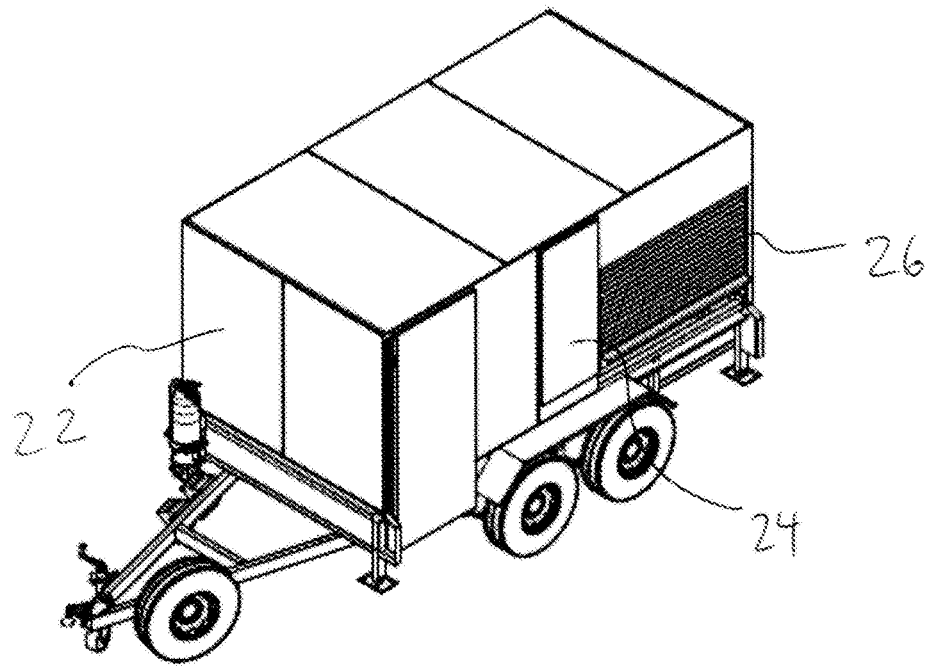

In exemplary aspects, and with reference to FIGS. 5-6, two data networks can be installed and configured inside the core analysis system. A first data network, shown as the TrailerControlNET in FIG. 5, can provide network services for automation components. It is contemplated that the TrailerControlNET can be isolated from other networks to ensure security and deterministic performance attributes needed by control networks. A second data network, shown as the TrailerDataNET in FIG. 5, can supply a data network required to push large data sets from the IPC to the IDC at designated cycle points. The IPC can use the TrailerDataNET network to retrieve calibration and setup files delivered to the IDC by a system engineer. In use, it is contemplated that remote access connections to the IPC and IDC also pass over the TrailerDataNET.

In exemplary aspects, the core analysis system can further comprise a CorporateServiceNET network that provides VPN access from the Network Router on the TrailerDataNET to a WAN authentication/access service.

Optionally, in exemplary aspects, the IDC can be an industrial grade computer configured to operate as a "Data Concentrator" node on the TrailerDataNet. In use, it is contemplated that the operator does not directly interface with the IDC through the local user interface 170 but can monitor logs that show transfer of core data from the IPC to the IDC. In use, it is further contemplated that the database used on the IDC can bridge data from each remote XRF Trailer system into a centralized data warehouse.

Core Analysis Methods

In use, and as further disclosed herein, the core analysis system 10 can be used to perform a core analysis method. In one aspect, a core analysis method can comprise positioning the trailer in a selected position relative to a drill location. In this aspect, and as further disclosed herein, the analysis assembly can be secured to the trailer. In another aspect, the core analysis method can further comprise positioning one or more core samples on the conveyor subassembly. In an additional aspect, the core analysis method can comprise activating the conveyor subassembly to selectively deliver the one or more core samples to the sample analysis area of the XRF detection subassembly. In a further aspect, the core analysis method can comprise activating the XRF detection subassembly while the one or more core samples are positioned in the sample analysis area.

In exemplary aspects, and as further disclosed herein, when the XRF detection subassembly comprises an X-ray source and an XRF sensor, the X-ray source can deliver radiation to the one or more core samples positioned within the sample analysis area. In these aspects, the core analysis method can comprise using the XRF sensor to detect X-ray fluorescence in response to the radiation delivered to the core samples by the X-ray source.

In further exemplary aspects, the core analysis method can comprise using the conveyor subassembly to selectively advance the one or more core samples between the sample loading location and the sample unloading location. In these aspects, the XRF detection subassembly can be positioned between the sample loading location and the sample unloading location.

In still further exemplary aspects, the core analysis method can comprise using the conveyor subassembly to selectively advance the one or more core samples relative to the first axis between the sample loading location and the sample unloading location. In these aspects, and as further disclosed herein, the XRF detection subassembly can be positioned between the sample loading location and the sample unloading location relative to the first axis.

In still further exemplary aspects, and as further disclosed herein, the sample analysis area of the XRF detection subassembly can be spaced from the first axis relative to a second axis. In these aspects, the core analysis method can comprise using the conveyor subassembly to selectively advance the one or more core samples relative to the second axis to deliver the one or more core samples to the sample analysis area of the XRF detection subassembly.

In further exemplary aspects, the core analysis method can further comprise, for each delivery of radiation to core samples positioned within the sample analysis area, using the processor to receive at least one output from the XRF sensor. In these aspects, and as further disclosed herein, the at least one output can be indicative of the measured XRF of the core samples positioned within the sample analysis area.

In further exemplary aspects, the core analysis method can comprise positioning one or more core samples within a container. In these aspects, the core analysis method can further comprise selectively delivering the at least one container to the sample analysis area of the XRF detection subassembly. Optionally, in additional aspects, each container can comprise indicia of at least one characteristic of the one or more core samples positioned within the container, and the method further comprises using an input imaging assembly to detect the indicia of each container, wherein the input imaging assembly is communicatively coupled to the processor. Optionally, in some aspects and as further disclosed herein, the input imaging assembly can be positioned proximate the sample loading location.

In still further exemplary aspects, the core analysis method can further comprise using a drying assembly to dry the one or more core samples. In these aspects, and as further disclosed herein, the drying assembly can be positioned between the sample loading location and the sample analysis area of the XRF detection subassembly. In additional aspects, when the processor is communicatively coupled to the drying assembly as disclosed herein, the core analysis method can further comprise using the processor to selectively activate the drying assembly to dry the one or more samples.

In still further exemplary aspects, when the XRF detection subassembly comprises a first imaging assembly as further disclosed herein, the core analysis method can further comprise using the first imaging assembly to produce an image of core samples received within the sample analysis area. In additional aspects, the core analysis method can comprise using the processor to selectively activate the first imaging assembly to produce an image of core samples within the sample analysis area.

In still further exemplary aspects, the core analysis method can further comprise using a wetting assembly to wet the one or more samples. Optionally, in these aspects, the wetting assembly can be positioned between the sample analysis area and the sample unloading location. In additional aspects, when the processor is communicatively coupled to the wetting assembly as further disclosed herein, the core analysis method can comprise using the processor to selectively activate the wetting assembly. Optionally, in further aspects, the core analysis method can further comprise using a second imaging assembly to produce an image of the one or more core samples following wetting of the one or more core samples. In these aspects, and as further disclosed herein, it is contemplated that the second imaging assembly can be positioned between the wetting assembly and the sample unloading location. In exemplary aspects, and as further disclosed herein, when the processor is communicatively coupled to the second imaging assembly, the core analysis method can comprise using the processor to selectively activate the second imaging assembly.

In still further exemplary aspects, the core analysis method can further comprise using the drive mechanism of the conveyor subassembly to power (and effect) movement of the intermediate sections of the conveyor subassembly. Optionally, in these aspects, using the drive mechanism to power movement of the intermediate sections can comprise: using at least one intermediate section to advance the one or more core samples relative to the first axis; and using at least one intermediate section to advance the one or more core samples relative to the second axis.

In still further exemplary aspects, and as further disclosed herein, the core analysis method can further comprise using the second wireless transmitter-receiver to receive information from the first wireless transmitter-receiver and to transmit information from the database to the first wireless transmitter-receiver.

In still further exemplary aspects, and as further disclosed herein, the core analysis method can further comprise selectively accessing the database from at least one remote location.

In still further exemplary aspects, and as further disclosed herein, the core analysis method can further comprise using the user interface to receive one or more inputs from a user.

In use, it is contemplated that the processing elements of the disclosed core analysis methods can accomplish one or more of the following tasks: managing the orderly startup and shutdown of control and data collection functions; collecting system setup information from the operator using the user interface (e.g., touch-panel interface); controlling the movement of containers (e.g., core boxes) into and out of the system; identifying containers (e.g., core boxes) along with attributes associated with the contents of the containers; associating containers (e.g., core boxes) to images, XRF results, and instrument status information collected by the data acquisition components of the system; transmitting data sets to a central database using wireless networks; providing diagnostics to assist rapid detection and correction of upset conditions and failed components of the system; and controlling and monitoring trailer utilities (Power, HVAC, Helium Supply).

In exemplary aspects, it is contemplated that the disclosed systems and methods can permit processing of core samples in an automated or semi-automated manner. For example, in some optional aspects, automatic analysis cycles can be processed for a core sample container (e.g., core box) in the following sequence. First, a core container can be manually positioned by an operator at the input section (e.g., roller conveyor 60). Second, if the first intermediate conveyor section is empty, the core container can be indexed into the first intermediate conveyor section. With the core container positioned on the first intermediate conveyor section, the input imaging assembly 100 can be triggered to capture a core container image. The core container image can be presented to the operator through the user interface, and the operator can use the user interface to provide one or more of the following pieces of information: drill site project name (optionally, from drop-down list); core depth (at Reference 0 on the core container); and depth information associated with selected scan areas on the obtained image. After this information is collected, the operator can initiate the processing sequence (e.g., by clicking or selecting a "Process Core Box" button or equivalent.

Prior to use of the disclosed systems and methods (e.g., during commissioning), it is contemplated that the following data can be associated with each type of core container (e.g., core box) to be used with the core analysis system. Thus, when the system operator selects a particular core container type, the following data can be referenced during operation of the system: core length (maximum length of an individual row of core); number of core segments (number of core segments in a core container); core X-axis starting position; core X-axis ending position; core Y-axis segment position (taught for each segment in core container); core Z-axis slow position; and core Z-axis max position. Upon entry of this information, the information can be inserted into a log table within the memory 85, and the profile of each core container type can be selectively accessed for each core container that is passed through the system.

When processing begins, a record can be inserted into the memory with the operator-supplied information. If the second intermediate conveyor section 68b is empty, then the processor can initiate indexing of the core container onto the second intermediate conveyor section 68b. The processor can then activate the drying assembly, and upon detection of the core container on the second intermediate conveyor section 68b, the core container can be clamped such that the core container is coupled to the actuators of the drive assembly 70 that advance the core container within the sample analysis area. The processor can initiate movement of the core container into the sample analysis area relative to the first axis at a speed that is configured for optimal drying. As the core container exits the drying assembly and enters the core sample analysis area, the processor receives a signal indicative of the presence of the core container within the sample analysis area (e.g., through a proximity switch, encoder, or other sensor), and the processor can then activate imaging assembly 48 to capture a dry core sample image. The acquired image can then be provided to the memory and associated with the core container record. The processor can then send a signal that initiates the cycle of the XRF detection subassembly. The processor can be configured to activate a first actuator to move the XRF sensor and X-Ray source relative to the first axis 52 to an operative position proximate a first sample segment. The processor can be configured to then activate a second actuator to move the core container to a sampling location relative to the X-Ray source and XRF sensor. The processor can then activate imaging of the sample location using imaging assembly 190. If the particular analysis method employed requires helium, then the processor can be configured to activate flow of helium into the sample analysis area. With the core container in the sample location, the processor can be configured to activate an actuator to effect downward movement of the XRF sensor and other analysis components relative to a vertical axis until the core is contacted (or nearly contacted). Upon contact, the processor can initiate an assay with associated filter, energy, and duration parameters. The transmitted live spectrum can be collected and processed into a display. When the assay is completed, the processor can deactivate helium flow. RAW spectrum data can be requested, processed with the specified calibrations, and stored into the memory along with the sample image. Next, the actuator(s) can return the XRF sensor and other processing components to its initial (home) position. The sequence of movement relative to the first, second, and vertical axes can be repeated for each sample segment on the core container until all sample segments are processed.

After processing is completed, all core container data can be sent to the IDC as further disclosed herein. The processor can then send a signal to prepare the system for unloading of the core container. The processor can cause the core container to be returned to the second intermediate conveyor section, and the processor can receive a signal (from a sensor as disclosed herein) that is indicative of the presence of the core container at the second intermediate conveyor section. Upon receipt of a signal indicative of the presence of the core container, the processor can activate the wetting assembly 120 and initiate movement of the core container through the wetting assembly (from the second intermediate conveyor section to the third intermediate conveyor section 68c). The wetting assembly can then be deactivated, and the imaging assembly 130 can be triggered to capture a wet core sample image. The image can then be inserted into the memory and associated with the core container record. If the output section (roller conveyor 64) is empty, then the processor can cause indexing of the core container to the output section.

Thus, in use, the core analysis process can be fully automated from the point where the core container is loaded at the input section 58 to the point where the core container is retrieved at the output section 62. In exemplary aspects, it is contemplated that the system operator can input a depth range ("Depth From", "Depth To") and scan interval that are determined and disclosed to the drilling team. As further disclosed herein, the "field ready" automated scanner can be compatible with PQ, HQ, NQ and BQ core containers, which can be provided with drill rigs that make use of the XRF technology disclosed herein.

To monitor instrument drift, it is contemplated that variations of XRF concentrations of internationally recognized standards to that of refined laboratory methods can be monitored. In exemplary aspects, a variety of recognized standard core compositions can be used. It is contemplated that quality assurance/quality control protocols can be employed on a regular basis and constant with depth. In exemplary aspects, the standard core compositions can comprise any site matrix that is matched to required standards for a particular client. In these aspects, the standard core compositions can further comprise any reference standards used to create an empirical calibration as further disclosed herein. Optionally, the standard core compositions can be provided as pressed pellets that are formed by pressing pulverized rock material (at μm sizes) under pressure (e.g., 20 tonnes (metric tons)) to produce a solid briquette.

Figure 9A:
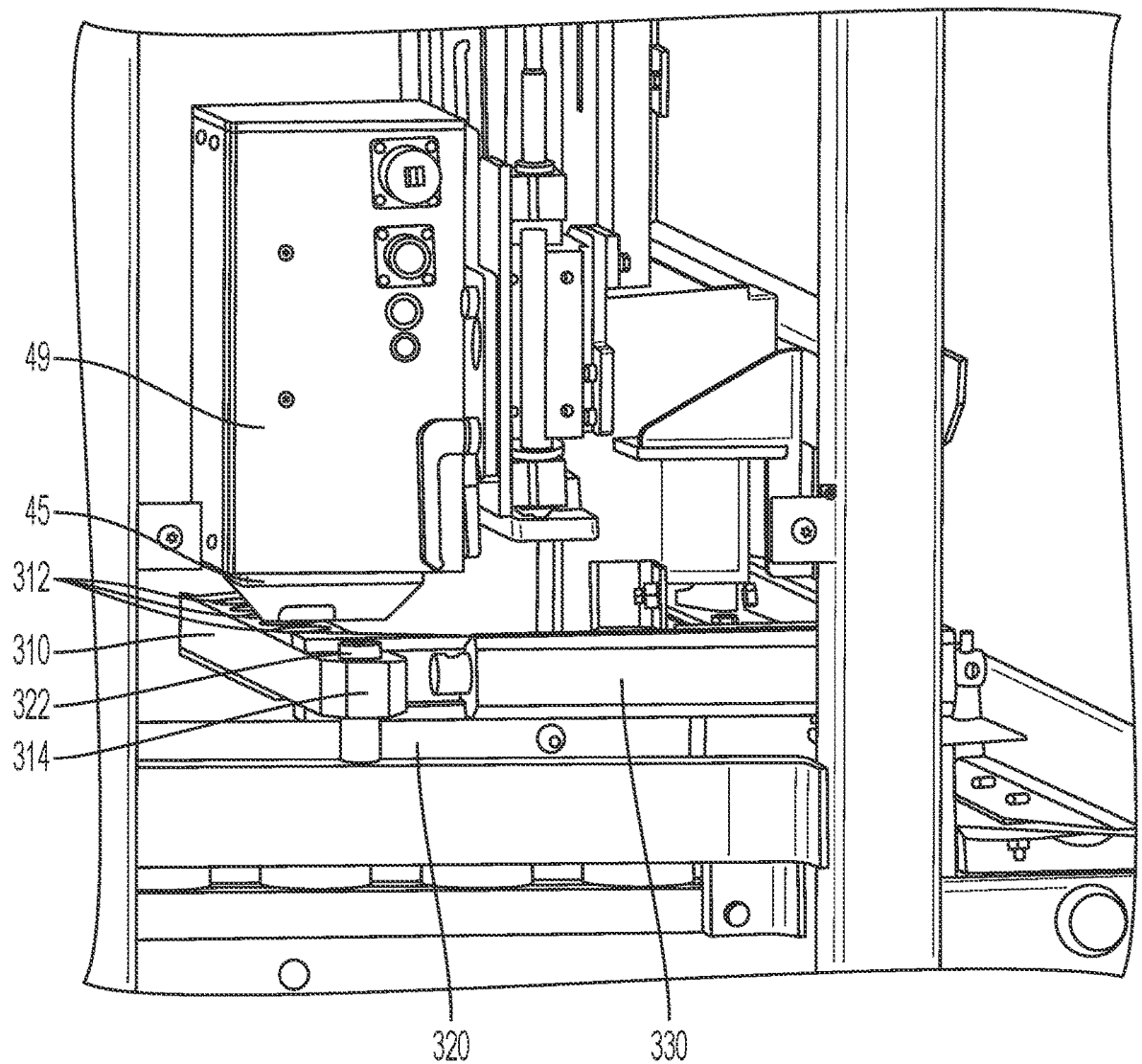
FIG. 9A is a side perspective view of an exemplary verification assembly as disclosed herein, with the arm of the verification assembly positioned in an operative "presentation" position.
Figure 9B:
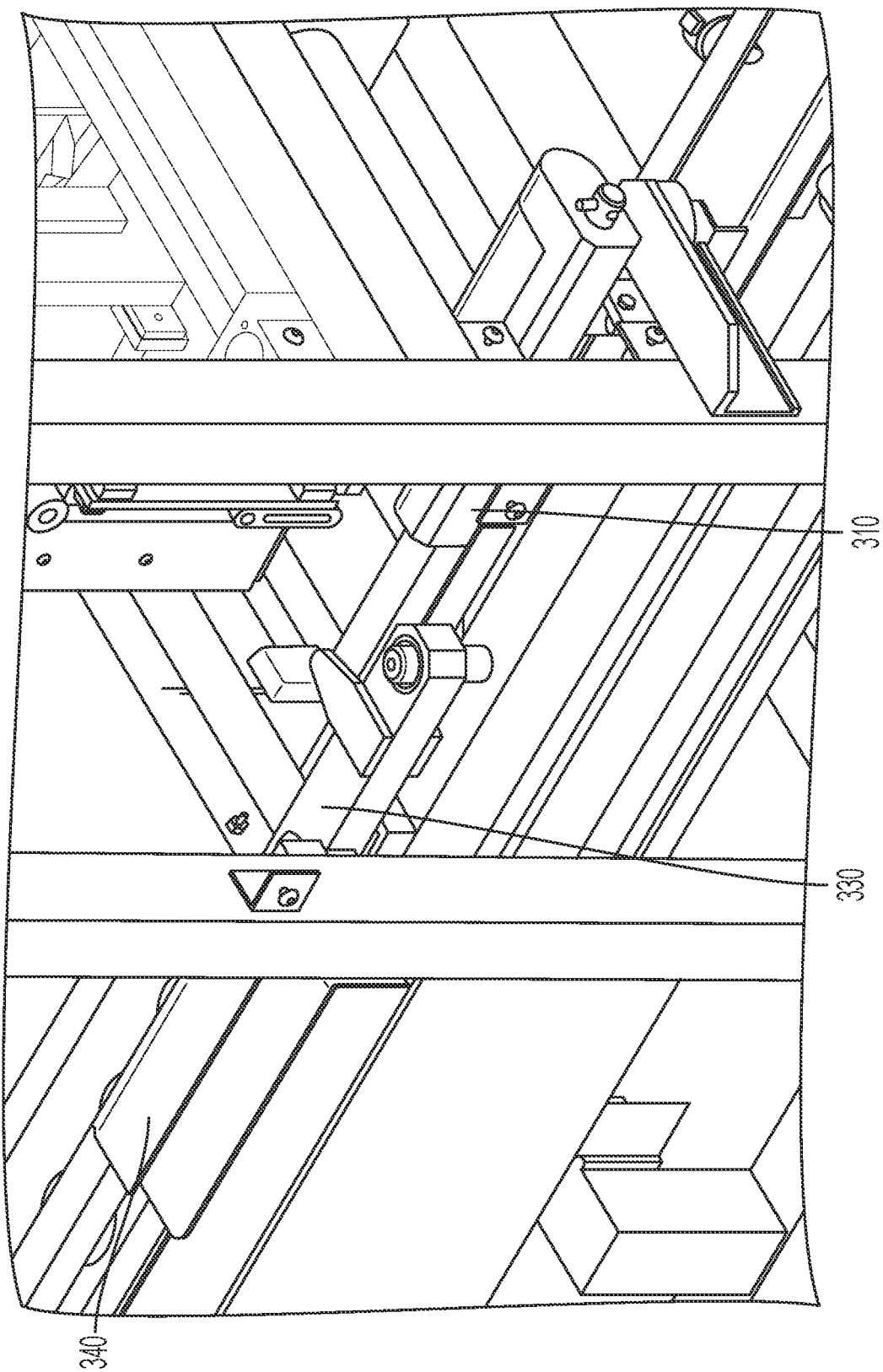
FIG. 9B is a side perspective view of the verification assembly of FIG. 9A, with the arm of the verification assembly positioned in a rest position (and the actuator associated with the arm in an extended position).
Figure 9C:
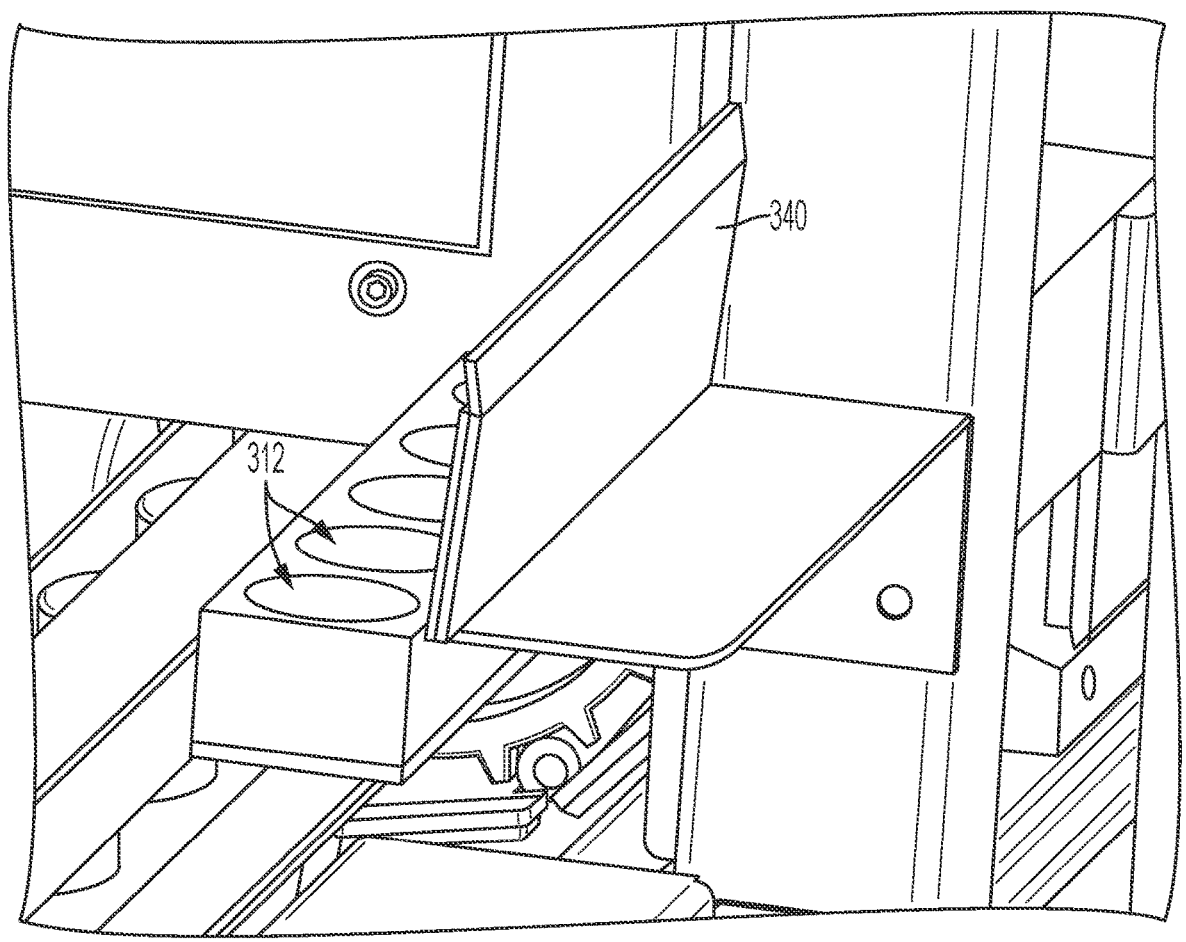
FIG. 9C is an end perspective view of the arm and the cover of the verification assembly of FIG. 9A as the arm approaches the cover (and prior to movement of the cover to enclose the receptacles of the arm).

In exemplary aspects, and with reference to FIGS. 9A-9C, a verification assembly 300 can be used to preserve the quality of data obtained by the system. In use, and as further described herein, the verification assembly 300 can be operated automatically with the XRF detection subassembly at regular intervals determined by a methods engineer. It is contemplated that the verification assembly 300 can be used as part of a formulated "Quality Control/Quality Assurance" program implemented on each project in an attempt to preserve data integrity. It is further contemplated that the data related to the analysis of "standard" trays (e.g., elemental concentration, name, location relative to the XRF detection assembly) can be recorded and associated with the verification assembly 300 in data tables for further processing and analysis. In exemplary aspects, the verification assembly 300 can be configured to periodically analyze a selection of one or more pellet samples (e.g., from one pellet up to six pellets) using the XRF assembly 40. The presentation of these pellets can be controlled by the database and software programs disclosed herein. Although the process can be selectively run in response to a manual input through the user interface, it is contemplated that the verification process can be scripted into an "Analysis Method" that includes the X-ray parameters, Project Metadata, and Machine parameters (e.g., Scan spacing), which can be linked through a "standards" table in the database. It is contemplated that the "standards" table can associate data for a particular "standard" sample with specific instruments, analysis methods, and other site characteristics. The disclosed verification method can optionally be initiated using the PLC 80b and the Trailer Services bloc in the network topology further disclosed herein. In use, the processor 80 can compare the parameters recorded during a given verification process to "standards" data or previously measured parameters to evaluate accuracy, precision, instrument drift, and contamination of the analysis assembly.

In use, the verification method can be a part of the normal use of the system, between box runs (normal operation scanning trays). In exemplary aspects, at least one pressed pellet (e.g, at least one 6×32 mm pressed pellet) can be positioned within receptacles 312 (optionally, axially aligned receptacles) of an arm 310 of the verification assembly 300. As used herein, the term "pellet" refers to "standard" material compositions, which can optionally comprise pulverized rock (80% passing grains less than 75 um) pressed into a small circular briquette to produce a sample that is representative of rock density for XRF analysis purposes. Each receptacle 312 can be in communication with a biased spring such that biases the pellets away from the receptacle (opposite the direction of gravity). Optionally, the receptacles 312 can be provided with an acrylic backing. In use, the receptacles ensure the pellet makes contact with the XMS apparatus by applying a reactionary force against the XMS pressing (due to gravity).

The arm 310 can have a proximal end 314 that is pivotally coupled to a pin/projection 322 of a support bar 320. The pin/projection 322 can extend upwardly from the support bar 320, and the arm 310 can pivot relative to a rotational axis that extends through the pin/projection and is parallel to a vertical axis. The arm 310 can be operatively coupled to an actuator 330 (e.g., a linear actuator) that is configured to effect pivotal movement of the arm about and between an operative "presentation" position and a rest position. As shown in FIGS. 9A-9B, it is contemplated that the actuator 330 can be retracted to pivot the arm 310 in the operative "presentation" position in which the XRF sensor can contact (or be positioned proximate) the receptacles 312. With the arm 310 in the "presentation" position, the pellets within the arm 310 can be individually and sequentially scanned as further disclosed herein. It is contemplated that the scans of the pellets can be performed at predetermined time intervals in accordance with the disclosed automated methods. In use, it is contemplated that the proximity sensor 47 of the XRF subassembly 40 can be configured to detect the presence of the arm 310 in the "presentation" position, at which point scanning of the pellets can be initiated.

After scanning of pellets is completed, the actuator 330 can be extended to pivot the arm 310 away from the operative position until reaching the rest position. In exemplary aspects, the verification assembly 300 can comprise a cover 340 that is configured for movement about and between a closed position and an open position. In the closed position, the cover 340 can be configured for placement over the receptacles 312 of the arm 310 when the arm is in the rest position. In operation, when the arm 310 reaches the rest position, the arm can press against a spring-loaded flange, which effects movement of the cover from the open position to the closed position. Alternatively (or additionally), a proximity sensor 342 can detect the presence of the arm 310 in the rest position, and in response to receipt of a signal from the processor 80 indicating the presence of the arm 310 in the rest position, a cover actuator 344 can effect movement of the cover 340 from the open position to the closed position, thereby enclosing the receptacles 312. Optionally, the cover 340 can be pivotally coupled to a portion of the frame 32, such as through a mount as shown in FIG. 9C.

In exemplary aspects, the pellets can reflect matrix-matched standards, such as certified reference materials (CRMs) or other reference materials used during calibration of the analysis assembly 30, thereby permitting monitoring of accuracy and instrument drift. In exemplary aspects, one of the pellets can comprise a silica blank that can be used for monitoring of contamination. Verification data can be stored in the database (e.g., a SQL database) and exported as part of Quality Assurance/Quality Control summary reports separate from the data recorded during regular core sample analysis. It is contemplated that the program can be modular, allowing for use of the verification process in accordance with the wants and needs of the customer.

In exemplary aspects, the pellets can reflect matrix-matched standards, such as certified reference materials (CRMs) or other reference materials used during calibration of the analysis assembly 30, thereby permitting monitoring of accuracy and instrument drift. In exemplary aspects, one of the pellets can comprise a silica blank that can be used for monitoring of contamination. Verification data can be stored in the database (e.g., a SQL database) and exported as part of Quality Assurance/Quality Control summary reports separate from the data recorded during regular core sample analysis. It is contemplated that the program can be modular, allowing for use of the verification process in accordance with the wants and needs of the customer.

In operation, it is contemplated that disclosed verification methods can provide for monitoring of accuracy, precision, instrument drift, and contamination of the system to ensure that quality assurance/quality control standards are met. During use, the processor 80 can initiate the verification method and present at least one pressed pellet sample to the XRF sensor. This is done at periodic intervals set by the Methods Engineer. When verification is initiated, during normal operation, it is contemplated that the HMI user interface can display a message such as "Verification In Progress." Next, the actuator 330 can retract, thereby presenting the pressed pellets to the sensor. As shown in FIG. 9A, the arm 310 can be in line with the XMS opening 45 when in the presented position. The proximity sensor 47 (or a separate proximity sensor within the sample analysis area) detects this, and the actuator 192 of the XRF subassembly 40 can lower the XMS housing 49 in a "Slow" speed to the arm 310, with the spring-loaded pellets pressing against the sensor and/or the housing, to a preset end point. The XMS assembly can then acquire XRF spectra from the pellet(s) and store data/meta data in appropriate tables. The actuators 192 can then lift the XMS housing and move the XMS housing along the first axis 52 to the next pellet (if any, up to 6 pellets), The total number of pellets will depend upon the number of pellets required for the particular QA/QC program. The analysis process can be repeated for each respective pellet. After all pellets are scanned, the actuator 330 can be extended to return the arm 310 to the rest position as shown in FIG. 9C, thereby effecting movement of the cover from the open position to the closed position, in which the pellets are protected contamination, damage and loss of the verification "Pellets" as further defined herein. During the transport of the analysis assembly 30, it is contemplated that the set of pellets can be provided as a verification slide that can be transported separately from the XMS assembly (e.g., in a pelican case), thereby eliminating any possibility of lost pellets, pellets being in the incorrect location for purposes of verification, and damage during transport. After the spectra acquisition data/parameters are recorded for the pellets, the processor can be configured to compare the recorded data/parameters to "standards" data/parameters or to previously recorded data/parameters for the pellets, and the processor can use this comparison to determine the accuracy, precision, instrument drift, and contamination of the analysis assembly.

Optionally, the disclosed system can provide a continuous scanning method (Drag Mode) as an alternative to the stop and start "Spot Scan" method disclosed herein. When a continuous scanning method is used, a selected row of core within a core box can be scanned in a continuous manner without halting the XRF acquisition process. The acquired data will therefore be representative of a full scanned meter (or other distance) of core rather than a series of single spot scans. To help perform the continuous scanning method, it is contemplated that the disclosed system can be provided with an ultrasonic transducer (UT) sensor that feeds a digital signal of "height" to allow for loop control of the Z axis to account for varying core heights. In addition, it is contemplated that a Z-axis actuator can be modified to be a "slow" or more precise actuator to permit maintenance of a precise gap between the core face and the instrument face.

Exemplary Aspects

In view of the described core analysis systems and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A core analysis system comprising: a trailer; and an analysis assembly secured to the trailer, wherein the analysis assembly comprises: an X-ray Fluorescence (XRF) detection subassembly defining a sample analysis area; and a conveyor subassembly configured to selectively deliver one or more core samples to the sample analysis area of the XRF detection subassembly.

Aspect 2: The core analysis system of aspect 1, wherein the XRF detection subassembly comprises: an X-ray source configured to deliver radiation to core samples positioned within the sample analysis area; and an XRF sensor configured to detect X-ray fluorescence in response to the radiation delivered to the core samples by the X-ray source.

Aspect 3: The core analysis system of any one of the preceding aspects, wherein the conveyor subassembly is configured to selectively advance one or more core samples between a sample loading location and a sample unloading location, and wherein the XRF detection subassembly is positioned between the sample loading location and the sample unloading location.

Aspect 4: The core analysis system of aspect 3, wherein the conveyor subassembly is configured to selectively advance the one or more core samples relative to a first axis between the sample loading location and the sample unloading location, and wherein the XRF detection subassembly is positioned between the sample loading location and the sample unloading location relative to the first axis.

Aspect 5: The core analysis system of aspect 4, wherein the sample analysis area of the XRF detection subassembly is spaced from the first axis relative to a second axis, wherein the conveyor subassembly is configured to selectively advance the one or more core samples relative to the second axis to deliver the one or more core samples to the sample analysis area of the XRF detection subassembly.

Aspect 6: The core analysis system of aspect 5, wherein, within a plane containing the first and second axes, the second axis is substantially perpendicular to the first axis.

Aspect 7: The core analysis system of any one of aspects 3-6, further comprising a processor communicatively coupled to the XRF detection subassembly, wherein for each delivery of radiation to core samples positioned within the sample analysis area, the processor is configured to receive at least one output from the XRF sensor, wherein the at least one output is indicative of the measured XRF of the core samples positioned within the sample analysis area.

Aspect 8: The core analysis system of aspect 7, further comprising at least one container configured to receive one or more core samples, and wherein the conveyor subassembly is configured to selectively deliver the at least one container to the sample analysis area of the XRF detection subassembly.

Aspect 9: The core analysis system of aspect 8, wherein each container comprises indicia of at least one characteristic of the one or more core samples positioned within the container, and wherein the core analysis system further comprises an input imaging assembly that is communicatively coupled to the processor and configured to detect the indicia of each container.

Aspect 10: The core analysis system of aspect 9, wherein the input imaging assembly is positioned proximate the sample loading location.

Aspect 11: The core analysis system of aspect 9 or aspect 10, wherein the indicia of each container comprises at least one bar code, and wherein the input imaging assembly comprises a bar code scanner.

Aspect 12: The core analysis system of aspect 9 or aspect 10, wherein the indicia of each container comprises a radiofrequency identification (RFID) tag, and wherein the input imaging assembly comprises an RFID scanner.

Aspect 13: The core analysis system of any one of aspects 7-12, further comprising a drying assembly positioned between the sample loading location and the sample analysis area of the XRF detection subassembly.

Aspect 14: The core analysis system of aspect 13, wherein the processor is communicatively coupled to the drying assembly, and wherein the processor is configured to selectively activate the drying assembly.

Aspect 15: The core analysis system of aspect 13 or aspect 14, wherein the XRF detection subassembly comprises a first imaging assembly, wherein the first imaging assembly is configured to produce an image of core samples received within the sample analysis area.

Aspect 16: The core analysis system of aspect 15, wherein the processor is configured to selectively activate the first imaging assembly to produce an image of core samples within the sample analysis area.

Aspect 17: The core analysis system of aspect 15 or aspect 16, further comprising a wetting assembly positioned between the sample analysis area and the sample unloading location.

Aspect 18: The core analysis system of aspect 17, wherein the processor is communicatively coupled to the wetting assembly, and wherein the processor is configured to selectively activate the wetting assembly.

Aspect 19: The core analysis system of aspect 17 or aspect 18, further comprising a second imaging assembly positioned between the wetting assembly and the sample unloading location.

Aspect 20: The core analysis system of aspect 19, wherein the processor is communicatively coupled to the second imaging assembly, and wherein the processor is configured to selectively activate the second imaging assembly.

Aspect 21: The core analysis system of any one of the preceding aspects, wherein the conveyor subassembly comprises: input and output sections comprising roller conveyors, wherein the input section defines the sample loading location, wherein the output section defines the sample unloading location; a plurality of intermediate sections positioned between the input and output sections; and a drive mechanism configured to power movement of the intermediate sections.

Aspect 22: The core analysis system of aspect 21, wherein the plurality of intermediate sections comprises: at least one intermediate section configured to advance the one or more core samples relative to the first axis; and at least one intermediate section configured to advance the one or more core samples relative to the second axis.

Aspect 23: The core analysis system of any one of the preceding aspects, wherein the analysis assembly further comprises a first wireless transmitter-receiver communicatively coupled to the processor.

Aspect 24: The core analysis system of aspect 23, further comprising: a database; and a second wireless transmitter-receiver communicatively coupled to the database, wherein the second wireless transmitter-receiver is configured to receive information from the first wireless transmitter-receiver and to transmit information from the database to the first wireless transmitter-receiver.

Aspect 25: The core analysis system of aspect 24, wherein the database is selectively remotely accessible.

Aspect 26: The core analysis system of any one of aspects 7-25, further comprising a user interface, wherein the processor is communicatively coupled to the user interface and configured to receive one or more inputs from the user interface.

Aspect 27: A core analysis method comprising: positioning a trailer in a selected position relative to a drill location, wherein an analysis assembly is secured to the trailer, wherein the analysis assembly comprises: an X-ray Fluorescence (XRF) detection subassembly defining a sample analysis area; and a conveyor subassembly; positioning one or more core samples on the conveyor subassembly; activating the conveyor subassembly to electively deliver the one or more core samples to the sample analysis area of the XRF detection subassembly; and activating the XRF detection subassembly while the one or more core samples are positioned in the sample analysis area.

Aspect 28: The core analysis method of aspect 27, wherein the XRF detection subassembly comprises an X-ray source and an XRF sensor, wherein the X-ray source delivers radiation to the one or more core samples positioned within the sample analysis area, and wherein the XRF sensor detects X-ray fluorescence in response to the radiation delivered to the core samples by the X-ray source.

Aspect 29: The core analysis method of any one of aspects 27-28, wherein the conveyor subassembly selectively advances the one or more core samples between a sample loading location and a sample unloading location, and wherein the XRF detection subassembly is positioned between the sample loading location and the sample unloading location.

Aspect 30: The core analysis method of aspect 29, wherein the conveyor subassembly selectively advances the one or more core samples relative to a first axis between the sample loading location and the sample unloading location, and wherein the XRF detection subassembly is positioned between the sample loading location and the sample unloading location relative to the first axis.

Aspect 31: The core analysis method of aspect 30, wherein the sample analysis area of the XRF detection subassembly is spaced from the first axis relative to a second axis, wherein the conveyor subassembly selectively advances the one or more core samples relative to the second axis to deliver the one or more core samples to the sample analysis area of the XRF detection subassembly.

Aspect 32: The core analysis method of any one of aspects 30-31, wherein, within a plane containing the first and second axes, the second axis is substantially perpendicular to the first axis.

Aspect 33: The core analysis method of any one of aspects 27-32, further comprising a processor communicatively coupled to the XRF detection subassembly, wherein for each delivery of radiation to core samples positioned within the sample analysis area, the processor receives at least one output from the XRF sensor, wherein the at least one output is indicative of the measured XRF of the core samples positioned within the sample analysis area.

Aspect 34: The core analysis method of aspect 33, wherein the one or more core samples are positioned within a container, and wherein the conveyor subassembly selectively delivers the at least one container to the sample analysis area of the XRF detection subassembly.

Aspect 35: The core analysis method of aspect 34, wherein each container comprises indicia of at least one characteristic of the one or more core samples positioned within the container, and wherein the method further comprises using an input imaging assembly to detect the indicia of each container, wherein the input imaging assembly is communicatively coupled to the processor.

Aspect 36: The core analysis method of aspect 35, wherein the input imaging assembly is positioned proximate the sample loading location.

Aspect 37: The core analysis method of any one of aspects 35-36, wherein the indicia of each container comprises at least one bar code, and wherein the input imaging assembly comprises a bar code scanner.

Aspect 38: The core analysis method of any one of aspects 35-37, wherein the indicia of each container comprises a radiofrequency identification (RFID) tag, and wherein the input imaging assembly comprises an RFID scanner.

Aspect 39: The core analysis method of any one of aspects 33-38, further comprising using a drying assembly to dry the one or more core samples, wherein the drying assembly is positioned between the sample loading location and the sample analysis area of the XRF detection subassembly.

Aspect 40: The core analysis method of aspect 39, wherein the processor is communicatively coupled to the drying assembly, and wherein the processor selectively activates the drying assembly to dry the one or more samples.

Aspect 41: The core analysis method of any one of aspects 39-40, wherein the XRF detection subassembly comprises a first imaging assembly, and wherein the method further comprises using the first imaging assembly to produce an image of core samples received within the sample analysis area.

Aspect 42: The core analysis method of aspect 41, wherein the processor selectively activates the first imaging assembly to produce an image of core samples within the sample analysis area.

Aspect 43: The core analysis method of any one of aspects 41-42, further comprising using a wetting assembly to wet the one or more samples, wherein the wetting assembly is positioned between the sample analysis area and the sample unloading location.

Aspect 44: The core analysis method of aspect 43, wherein the processor is communicatively coupled to the wetting assembly, and wherein the processor selectively activates the wetting assembly.

Aspect 45: The core analysis method of aspect 44, further comprising using a second imaging assembly to produce an image of the one or more core samples following wetting of the one or more core samples, wherein the second imaging assembly is positioned between the wetting assembly and the sample unloading location.

Aspect 46: The core analysis method of aspect 45, wherein the processor is communicatively coupled to the second imaging assembly, and wherein the processor selectively activates the second imaging assembly.

Aspect 47: The core analysis method of any one of aspects 31-46, wherein the conveyor subassembly comprises: input and output sections comprising roller conveyors, wherein the input section defines the sample loading location, wherein the output section defines the sample unloading location; a plurality of intermediate sections positioned between the input and output sections; and a drive mechanism coupled to the intermediate sections, wherein the method further comprises using the drive mechanism to power movement of the intermediate sections.

Aspect 48: The core analysis method of aspect 47, wherein using the drive mechanism to power movement of the intermediate sections comprises: using at least one intermediate section to advance the one or more core samples relative to the first axis; and using at least one intermediate section to advance the one or more core samples relative to the second axis.

Aspect 49: The core analysis method of any one of aspects 33-48, wherein the analysis assembly further comprises a first wireless transmitter-receiver communicatively coupled to the processor.

Aspect 50: The core analysis method of aspect 49, wherein a second wireless transmitter-receiver is communicatively coupled to the database, and wherein the method further comprises using the second wireless transmitter-receiver to receive information from the first wireless transmitter-receiver and to transmit information from the database to the first wireless transmitter-receiver.

Aspect 51: The core analysis method of aspect 50, further comprising selectively accessing the database from at least one remote location.

Aspect 52: The core analysis method of any one of aspects 33-51, further comprising using a user interface to receive one or more inputs from a user, wherein the processor is communicatively coupled to the user interface.

Aspect 53: A core analysis assembly as disclosed herein.

Aspect 54: A core analysis assembly comprising: an X-ray Fluorescence (XRF) detection subassembly defining a sample analysis area; and a conveyor subassembly configured to selectively deliver one or more core samples to the sample analysis area of the XRF detection subassembly as disclosed herein.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

What is claimed is:

1. A method comprising:
    acquiring, by an imaging assembly, an image of chips within a core tray, the chips comprising core or rock material;
    receiving the core tray within a sample analysis area of an analysis assembly, the analysis assembly comprising:
        an X-ray Fluorescence (XRF) detection subassembly defining a sample analysis area, wherein the XRF detection subassembly comprises:
            an X-ray source; and
            an XRF sensor; and
        at least one processor communicatively coupled to the XRF detection subassembly;
    activating the X-ray source while the core tray is positioned in the sample analysis area, thereby delivering radiation to the chips within the core tray;
    detecting, by the XRF sensor, X-ray fluorescence in response to the radiation delivered to the chips by the X-ray source; and
    receiving, by the at least one processor, for each delivery of radiation to the chips positioned within the sample analysis area, at least one output from the XRF sensor, wherein the at least one output is indicative of the measured XRF of the chips positioned within the sample analysis area.

2. The method of claim 1, further comprising:
    performing reverse circulation drilling operations to produce chips comprising core or rock material; and
    positioning the chips within the core tray.

3. The method of claim 2, further comprising loading the core tray onto a sample loading location of a sample movement pathway.

4. The method of claim 3, wherein receiving the core tray within the sample analysis area comprises advancing the core tray from the sample loading location to the sample analysis area.

5. The method of claim 4, further comprising, following delivery of radiation to the chips within the core tray, advancing the core tray from the sample analysis area to a sample unloading location of the sample movement pathway.

6. The method of claim 5, wherein the sample unloading location is different than the sample loading location.

7. The method of claim 2, further comprising adjusting a vertical position of the X-ray source and the XRF sensor.

8. The method of claim 7, further comprising determining, by a second sensor, a vertical position of the chips within the sample analysis area, and wherein the vertical position of the X-ray source and the XRF sensor is adjusted based on the vertical position of the chips within the sample analysis area.

9. The method of claim 8, wherein the second sensor is an ultrasonic transducer.

10. The method of claim 2, further comprising maintaining, using an HVAC unit, a temperature within the sample analysis area at a desired level.

11. The method of claim 10, further comprising logging, using an environmental monitoring device, temperature variations within the sample analysis area.

12. The method of claim 2, further comprising supplying Helium gas to the XRF detection subassembly.

13. The method of claim 2, further comprising:
    receiving, from a first wireless transmitter-receiver communicatively coupled to the at least one processor, by a second wireless transmitter-receiver communicatively coupled to a database, information indicative of the measured XRF of the chips positioned within the sample analysis area.

14. The method of claim 13, further comprising:
    transmitting, from the second wireless transmitter-receiver, information from the database to the first wireless transmitter-receiver.

15. The method of claim 13, wherein the database is a centralized database that includes respective data sets acquired from a plurality of analysis assemblies that acquire XRF data.

16. The method of claim 2, wherein the analysis assembly is positioned at a site of the reverse drilling operations.

17. The method of claim 1, further comprising loading the core tray onto a sample loading location of a sample movement pathway.

18. The method of claim 17, wherein receiving the core tray within the sample analysis area comprises advancing the core tray from the sample loading location to the sample analysis area.

19. The method of claim 18, further comprising, following delivery of radiation to the chips within the core tray, advancing the core tray from the sample analysis area to a sample unloading location of the sample movement pathway.

20. The method of claim 19, wherein the sample unloading location is different than the sample loading location.

21. The method of claim 1, further comprising adjusting a vertical position of the X-ray source and the XRF sensor.

22. The method of claim 21, further comprising determining, by a second sensor, a vertical position of the chips within the sample analysis area, and wherein the vertical position of the X-ray source and the XRF sensor is adjusted based on the vertical position of the chips within the sample analysis area.

23. The method of claim 22, wherein the second sensor is an ultrasonic transducer.

24. The method of claim 1, further comprising maintaining, using an HVAC unit, a temperature within the sample analysis area at a desired level.

25. The method of claim 24, further comprising logging, using an environmental monitoring device, temperature variations within the sample analysis area.

26. The method of claim 1, further comprising supplying Helium gas to the XRF detection subassembly.

27. The method of claim 1, further comprising:
receiving, from a first wireless transmitter-receiver communicatively coupled to the at least one processor, by a second wireless transmitter-receiver communicatively coupled to a database, information indicative of the measured XRF of the chips positioned within the sample analysis area.

28. The method of claim 27, further comprising:
transmitting, from the second wireless transmitter-receiver, information from the database to the first wireless transmitter-receiver.

29. The method of claim 27, wherein the database is a centralized database that includes respective data sets acquired from a plurality of analysis assemblies that acquire XRF data.

* * * * *